United States Patent [19]
Atwater et al.

[11] Patent Number: 5,910,448
[45] Date of Patent: *Jun. 8, 1999

[54] PROCESS FOR ANALYZING $CO_2$ IN AIR AND IN WATER

[75] Inventors: James E. Atwater, Eugene; James R. Akse, Roseburg; Jeffrey DeHart, Yoncalla, all of Oreg.

[73] Assignee: Umpqua Research Company, Myrtle Creek, Oreg.

[ * ] Notice: This patent is subject to a terminal disclaimer.

[21] Appl. No.: 08/826,645

[22] Filed: Apr. 4, 1997

Related U.S. Application Data

[63] Continuation-in-part of application No. 08/332,570, Oct. 31, 1994, Pat. No. 5,643,799.

[51] Int. Cl.[6] .................................................. G01N 33/18
[52] U.S. Cl. .......................... 436/133; 436/150; 436/178; 422/82.02; 73/61.41
[58] Field of Search ..................................... 436/133, 150, 436/178, 181; 422/68.1, 82.01, 82.02, 88, 90; 73/61.41, 61.55

[56] References Cited

U.S. PATENT DOCUMENTS

| | | | |
|---|---|---|---|
| 3,855,001 | 12/1974 | Cheron | 136/86 C |
| 4,209,299 | 6/1980 | Carlson . | |
| 4,285,918 | 8/1981 | Gustafson | 423/228 |
| 4,293,522 | 10/1981 | Winkler | 422/80 |
| 4,892,383 | 1/1990 | Klainer et al. | 350/96.29 |
| 5,068,090 | 11/1991 | Connolly | 422/82.02 |
| 5,082,471 | 1/1992 | Athayde et al. | 55/16 |
| 5,132,094 | 7/1992 | Godec et al. | 422/68.1 |
| 5,281,254 | 1/1994 | Birbara et al. | 95/44 |

OTHER PUBLICATIONS

Title: Approximate Simulation of CO2 and H2S Absorption into Aqueous Alkanolamines; AlChE Journal, Aug. 1993, vol. 39. No. 8. By: David A. Glasscock and Gary T. Rochelle.

Title: A Mathmatical Model for Equilibrium Solubility of Hyrogen Sulfide and Carbon Diode in Aqueous Alkanolamine Solutions; Chemical Engineering Science vol. 36, pp. 355–362, By: R.D. Deshmukh and A.E. Mather.

Title: Correlation and Prediction of the Solubility of Carbon dioxide in a Mixed Alkanolamine Solution; Ind. Eng. Chem. Res 1994,33,2006–2015; By: Yi–Gui Li and Alan E. Mather.

Title: Diffusion Coefficients of Several Aqueous Alkanolamine Solutions; J.Chem Eng. Data 1993, By: Erwin De. Snijder, Marcel J.M. te Riele, Geert F. Versteeg and W.P.M. van Swaaij.

(List continued on next page.)

*Primary Examiner*—Jeffrey Snay
*Attorney, Agent, or Firm*—Marger Johnson McCollom & Stolowitz, P.C.

[57] ABSTRACT

The process of this invention comprises providing a membrane for separating $CO_2$ into a first $CO_2$ sample phase and a second $CO_2$ analyte phase. $CO_2$ is then transported through the membrane thereby separating the $CO_2$ with the membrane into a first $CO_2$ sample phase and a second $CO_2$ analyte liquid phase including an ionized, conductive, dissociated $CO_2$ species. Next, the concentration of the ionized, conductive, dissociated $CO_2$ species in the second $CO_2$ analyte liquid phase is chemically amplified using a water-soluble chemical reagent which reversibly reacts with undissociated $CO_2$ to produce conductivity changes therein corresponding to fluctuations in the partial pressure of $CO_2$ in the first $CO_2$ sample phase. Finally, the chemically amplified, ionized, conductive, dissociated $CO_2$ species is introduced to a conductivity measuring instrument. Conductivity changes in the chemically amplified, ionized, conductive, dissociated $CO_2$ species are detected using the conductivity measuring instrument.

18 Claims, 21 Drawing Sheets

OTHER PUBLICATIONS

Title: The Solubility of H2S and CO2 in Aqueous Monoethanolamine Solutions; The Canadian Journal of Chemical Engineering, vol. 52, Dec. 1974; By; J.I. Lee, F.D. Otto and A.E. Mather.

Title: The Solubility of Carbon Dioxide and Hydorgen Sulfide in a 35% Aqueous Solution of Methyldiethanolamine; The Canadian Journal of Chemical Engineering, vol. 71, Apr. 1993; By: Fang–Yuan Jou, John J. Carroll, Alan E. Mather and Frederick D. Otto.

Title: Kinetics fo CO2 with Primary and Secondary amines in Aqueous Solutions–I. Zwitteroin Deprotonation Kinetics for DEA and DIPA in Aqueiosu Blends of Alkanolamines; Chemical Engineering Science, vol. 47, No. 8, pp. 2027–2035, 1992; byL R.J. Littel, G.F. Versteeg and W.P.M. Van Swaaij.

Title: Solubility of Carbon Dioxide and Hydrogen Sulfide in Aqueious Alkanolamines; Ind. Eng. Chem. Res, 1993, 32, 1419–1430; By: Ralph H. Weiland, Tanmoy Chakravarty, and Alan E. Mather.

Title: Solubility and Diffusivity Data for the Absorption of COS, Co2 and N20 in Amine Solutions; J. Chem Eng. Data, 1992, 37, 49–55; By: Rob J. Littel, Geert F. Versteeg and Wim P.M. van Swaaij.

Title: Kinetics of Carbon Dioxide with Tertiary Amines in Aquious Solutions; AlChE, Journal, Nov. 1990, vol. 36, No. 11; by: R.J. Littel, W.P.M.van Swaaij and g.F. Versteeg.

Title: Absorption of Carbon Dioxide into Aqueous Solutions of Triethanolamine: AlChE Journal, Aug. 1990, vol. 36, No. 8; By: Jose I. Sotel; F. Javier Benitez, Jesus Beltran–Heredia, Concepcion Rodriguez.

Title: Vapor–Liquid Equilibrium of Carbon Dioxide in Aqueous Mixtures of Monothanolamine and Methnyldiethanolamine; I&EC Research, 1994, 33; By: Fang–Yuan Jou, Frederick D. Otto, and Alan E. Mather.

Title: Kinetics of Carbon Dioxide Ab sorption in Aqueous Solutions of Diisopropanolamine; Chem, Eng. Technol 15 (1992) 114–118; By: Jose L. Soltelo, F. Javier Benitez,Jesus Beltran–Heredia and Concepcion Rodrique.

Title: Solubility of H2S and CO2 in Aquious Methyldiethanolamine Solutios; Ind. Eng. Chem, Process Des.Dev 1982, 21, 539–544; By: Fang–Yuan Jou, Alan E. Mather, and Frederick D. Otto.

Title: Kinetics of CO2 with Primary and Secondary Amines n Aquious Solutons–II. Influence of Temperature on Zwitterion Formation and Deprotonation Rates; Chemical Engineering Science, vol. 47, No. 8 pp. 2037–2045, 1992; By: R.J. Littel,G.F. Versteeg and W.P.M. Van Swaaij.

a) CLOSED CIRCUIT b) OPEN CIRCUIT

- ● ETHANOLAMINE
- ◆ N,N-DIMETHYLETHANOLAMINE
- ○ DIETHANOLAMINE
- □ DIISOPROPANOLAMINE
- ▲ N-ETHYLDIETHANOLAMINE
- ▼ N-METHYLDIETHANOLAMINE
- ✱ TRIETHANOLAMINE

- ● ETHANOLAMINE
- ◆ N,N-DIMETHYLETHANOLAMINE
- ○ DIETHANOLAMINE
- □ DIISOPROPANOLAMINE
- ▲ N-ETHYLDIETHANOLAMINE
- ▼ N-METHYLDIETHANOLAMINE
- ✱ TRIETHANOLAMINE

- ETHANOLAMINE
- N,N-DIMETHYLETHANOLAMINE
- DIETHANOLAMINE
- DIISOPROPANOLAMINE
- N-ETHYLDIETHANOLAMINE
- N-METHYLDIETHANOLAMINE
- TRIETHANOLAMINE

- $10^{-3}$ M DIISOPROPANOLAMINE
- $10^{-3}$ M ETHANOLAMINE
- $10^{-3}$ M DIETHANOLAMINE
- DEIONIZED WATER

■ NON-POROUS SILOXANE
▲ MICROPOROUS POLYPROPYLENE
● NON-POROUS PTFE

- ● 50 MINUITES    ▫ 15 MINUITES
- ◆ 30 MINUITES    ■ 10 MINUITES
- ▼ 20 MINUITES    ⊙ 5 MINUITES

PROCESS FOR ANALYZING $CO_2$ IN AIR AND IN WATER

RELATED APPLICATION

This is a continuation-in-part of U.S. Ser. No. 08/332,570 filed on Oct. 31, 1994, now U.S. Pat. No. 5,643,799.

This invention was made with U.S. Government support under Grant Number DE-FG03-93ER81641 awarded by the Department of Energy. The U.S. Government has certain rights in the invention.

BACKGROUND OF THE INVENTION

The response of global climate to greenhouse gases, particularly $CO_2$, is of increasing concern to industrialized nations. International agreements concerning $CO_2$ emissions will have a major impact on governmental policy of advanced nations in the form of environmental regulation and industrialization policy. Atmospheric and oceanographic scientists are involved in detailed studies of the impact of $CO_2$ and other greenhouse gases on the global climate. Their findings will shape the direction the international community takes with regards to worldwide regulation of $CO_2$ emissions.

Scientific studies of global warming include predictive computer models as well as worldwide data collection. Projection of temperature trends suggest many alternative scenarios dependent on the rate of $CO_2$ increase. The $CO_2$ increase rate depends on the balance between its production and destruction by a variety of biological and physical processes which are presently poorly understood. Consequently, collection of $CO_2$ data is critical to evaluating and improving these climate models. Global profiles of highly accurate $CO_2$ data are needed. In particular, water, such as the oceans and other bodies of water, contain much more $CO_2$ than the atmosphere and may, in fact, act as a $CO_2$ sink or source. The flux of $CO_2$ across the air-water interface therefore becomes a very important parameter in determining the rate of change of $CO_2$ in the atmosphere.

Current processology relies on exacting sample collection and preparation, and time consuming analysis. The operation of gas chromatographic or infrared analyzers requires a dedicated analytical laboratory and expert personnel to attain the necessary level of accuracy and precision. These systems are also expensive, difficult to automate, require frequent calibration, are poorly suited to real time monitoring of $CO_2$ in water and/or air, and need constant maintenance. Most certainly, they are not well suited for wide scale, untended deployment in the large numbers necessary to provide data sufficient for a global profile.

Therefore a need exists for a sensor system capable of reliable, highly accurate analysis of $CO_2$ in air and/or water. This can include long term unattended analysis of $CO_2$ in air and/or water, particularly from aboard ship or mounted on buoys or other platforms.

SUMMARY OF THE INVENTION

The above described needs and others are met by the present invention, which is summarized and described in detail below. An air/water $CO_2$ analyzer system has been developed which satisfies the above-described needs using a unique process for determining the amount of $CO_2$. This process utilizes three basic steps for operation of the subject system, as follows: separating a $CO_2$ sample by transporting same through a membrane wherein the $CO_2$ sample is driven by concentration gradient differences to form a $CO_2$ analyte composition, chemical amplification of the concentration of ionized by-products of the $CO_2$ separation, and finally, specific conductance detection of the amplified $CO_2$.

The essence of the subject $CO_2$ analyzer technology lies in the chemical amplification of the conductivity signal associated with transport of $CO_2$ from an air or water source across a membrane into a control solution where ionization reactions occur. The control solution contains a chemical reagent which possesses a high absorptivity for $CO_2$, and which as part of the absorption mechanism reacts with $CO_2$ to form additional ionic species. For example, alkanolamines comprise a class of compounds which are water soluble, which absorb large amounts of $CO_2$, and which undergo ionization reactions. The chemical amplification of the conductivity response of these aqueous solutions will depend on kinetic factors such as contact time, temperature, membrane permeability, etc., the type and concentration of the reagent materials, and the $CO_2$ concentration. In a given analyzer module and measurement conditions, the conductivity response will be directly proportional to the $CO_2$ concentration and the response is detectable using existing flow through conductivity measuring devices.

More specifically, a process is provided for determining the concentration of $CO_2$ in air or in water. The process comprises providing a membrane for separating $CO_2$ into a first $CO_2$ sample phase and a second $CO_2$ analyte phase. $CO_2$ is then transported through the membrane thereby separating the $CO_2$ with the membrane into a first $CO_2$ sample phase and a second $CO_2$ analyte liquid phase including ionized, conductive, dissociated $CO_2$ species. Next, the concentration of the ionized, conductive, dissociated $CO_2$ species in the second $CO_2$ analyte liquid phase is chemically amplified using a water-soluble chemical reagent which reversibly reacts with undissociated $CO_2$ to produce conductivity changes therein corresponding to fluctuations in the partial pressure of $CO_2$ in the first $CO_2$ sample phase. Finally, the chemically amplified, ionized, conductive, dissociated $CO_2$ species is introduced to a conductivity measuring instrument. Conductivity changes in the chemically amplified, ionized, conductive, dissociated $CO_2$ species are detected using the conductivity measuring instrument. In the preferred process of this invention, $CO_2$ is transported through the membrane from an input side of the membrane to an output side of the membrane employing a differential concentration gradient in which the dissolved $CO_2$ concentration is higher on the input side of the membrane than on the output side of the membrane causing $CO_2$ to diffuse across the membrane.

The membrane is typically a microporous or non-porous membrane. The membrane materials for the non-porous membranes preferably comprise polytetrafluoroethylene, polydimethylsiloxane, and the membrane material for the microporous materials is microporous polypropylene, the microporous membranes preferably comprising polypropylene hollow fibers. In another form of this invention, the hollow fiber membrane comprises a coaxial tube within a tube arrangement for both gas-liquid and liquid-liquid $CO_2$ exchange.

The chemical reagent is typically an alkanolamine, preferably an alkanolamine selected from a group consisting of primary, secondary, and tertiary alkanolamines with two and three carbon alkanol groups, and more preferably an alkanolamine selected from a group consisting of diethanolamine, monoethanolamine, triethanolamine, N,N-dimethylethanolamine, N-methylethanolamine, N-ethylethanolamine, and diisopropanolamine.

Other preferred features include a process which is continuous, a process in which conductivity changes in the ionized, conductive, dissociated $CO_2$ species are determined even though unattended for extended periods of time, a process for analyzing $CO_2$ dissolved in seawater, and a process in which the conductivity measuring instrument is a flow-through instrument.

Other forms of the invention comprise the following: (1) a closed circuit configuration in which the chemical reagent solution continuously recirculates through the conductivity measuring instrument, and the chemical reagent solution either gaining or losing $CO_2$ across the membrane in order to equilibrate with a rising or falling $P_{CO_2}$ in the atmosphere or in the water, (2) an open circuit configuration in which chemical reagent solution flows from a feed reservoir, first through the membrane, then into the conductivity measuring instrument, and then to a waste repository, the chemical reagent being expendable and making a single pass through the system, and (3) a stopped flow injection configuration in which the chemical reagent is injected into the membrane contactor, the flow is stopped, and after a predetermined contact time, flow is re-established, a plug of $CO_2$-containing chemical reagent solution being displaced from the membrane, and then flowing through the conductivity measuring instrument. In the stopped-flow process, the contact time is preferably between about 5 and 30 minutes.

The preferred system for determining the concentration of $CO_2$ in air or in water, typically comprises a membrane for separating $CO_2$ into a first $CO_2$ sample phase and a second $CO_2$ analyte phase; means for transporting $CO_2$ through the membrane thereby separating the $CO_2$ with the membrane into a first $CO_2$ sample phase and a second $CO_2$ analyte liquid phase including an ionized, conductive, dissociated $CO_2$ species; means for chemically amplifying the concentration of the ionized, conductive, dissociated $CO_2$ species in the second $CO_2$ analyte liquid phase using a water-soluble chemical reagent which reversibly reacts with undissociated $CO_2$ to produce conductivity changes therein corresponding to fluctuations in the partial pressure of $CO_2$ in the first $CO_2$ sample phase; and a conductivity measuring instrument for receiving the chemically amplified, ionized, conductive, dissociated $CO_2$ species and detecting conductivity changes in the chemically amplified, ionized, conductive, dissociated $CO_2$ species.

DETAILED DESCRIPTION OF THE INVENTION

According to the present invention, there is provided an inexpensive, simple, reliable, and accurate means for continuous monitoring of $CO_2$ in the atmosphere and water, particularly seawater, with the capability for unattended operation over periods of deployment of up to one year. Operation of the analyzer is based upon previously-described three sequential operations: membrane transport, induced chemical amplification, and conductivity detection. Concentration gradients drive $CO_2$ transport from air or water across a membrane into an aqueous chemical reagent solution, typically an alkanolamine solution. $CO_2$ reacts with the dissolved chemical reagent forming charged species which are then detected using a conductivity cell.

Figure 1:
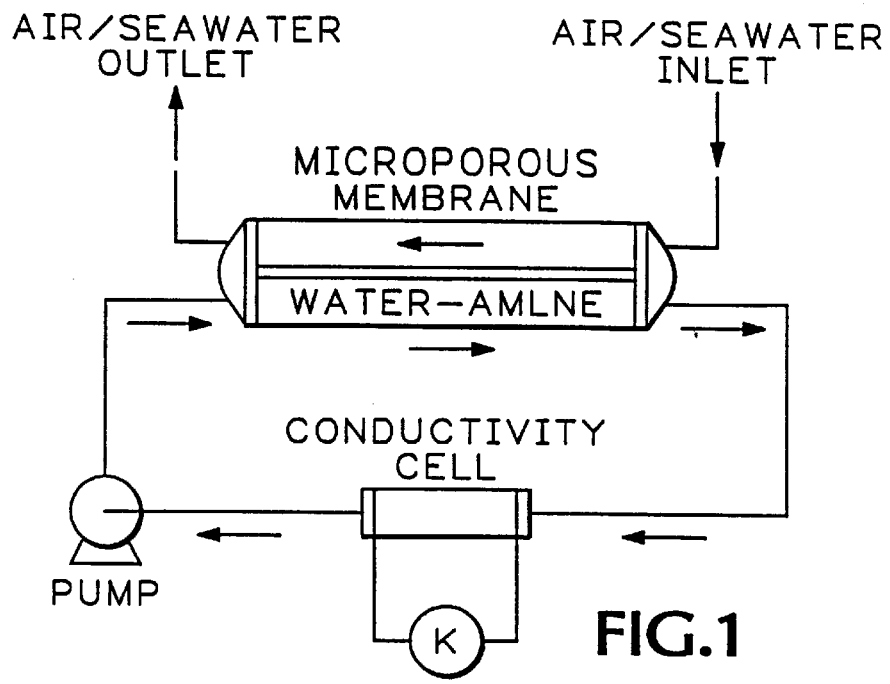
FIG. 1 is a flow schematic showing a $P_{CO_2}$ Analyzer.

One possible configuration of the $CO_2$ sensor is illustrated schematically in FIG. 1. $CO_2$ vapors readily transport across both non-porous and microporous hydrophobic membranes. When the membrane separates a gaseous and an aqueous phase, $CO_2$ will equilibrate across the membrane as in the following equation:

$$CO_2 \text{ (g)} \overset{H_{CO_2}}{\longleftrightarrow} CO_2 \text{ (aq)} \quad \text{(Eq. 1.1)}$$

The equilibrium between free gaseous $CO_2$ and dissolved $CO_2$ gas is described by Henry's Law, $$H_{CO_2} = \frac{P_{CO_2}}{m_{CO_2}} \frac{\text{atm-kg}}{\text{mol}} \quad \text{(Eq. 1.2)}$$

where $P\,CO_2$ is the partial pressure of $CO_2$ in the gas phase (atmospheres), $m_{CO_2}$ 2 is the molality (moles/kg) of $CO_2$ in the aqueous phase, and $H_{CO_2}$ is the Henry's Law constant for $CO_2$.

If the membrane separates two liquids, and the dissolved $CO_2$ concentration is higher in one liquid than the other, $CO_2$ will diffuse across the membrane until equal concentrations are established on both sides.

In water, ionic species originate from dissolved $CO_2$ via the dissociation reactions given in the following equations:

$$CO_2 + H_2O \overset{K_1}{\longleftrightarrow} H^+ + HCO_3^- \quad \text{(Eq. 1.3)}$$

$$HCO_3^- \overset{K_2}{\longleftrightarrow} H^+ + CO_3^{2-}. \quad \text{(Eq. 1.4)}$$

Figure 2:
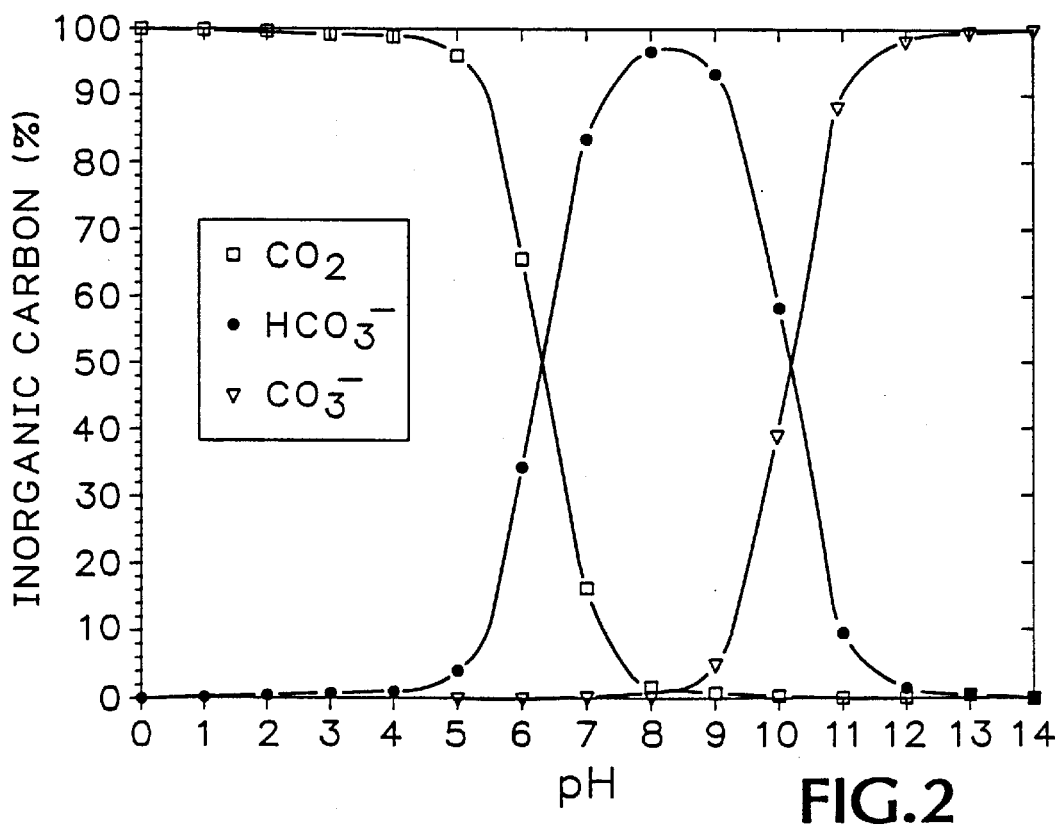
FIG. 2 is a graph showing Inorganic Carbon Speciation vs. pH for Deionized Water at 25 degrees C.

The extent of the resulting ionization is strongly pH dependent. The relationship between pH and inorganic carbon speciation at 25 degrees C. is shown for deionized water in FIG. 2. The dissociation of $CO_2$ produces hydrogen ions, which in the absence of buffering counter-ions, acidify the aqueous phase. For example, 300 $\mu$atm of $CO_2$(g) equilibrating with pure water of an initial pH=7 will produce a final pH of approximately 5.8. The ions formed by the dissociation of dissolved $CO_2$ increase the specific conductance (K) of the aqueous medium proportional to their concentrations.

Figure 3:
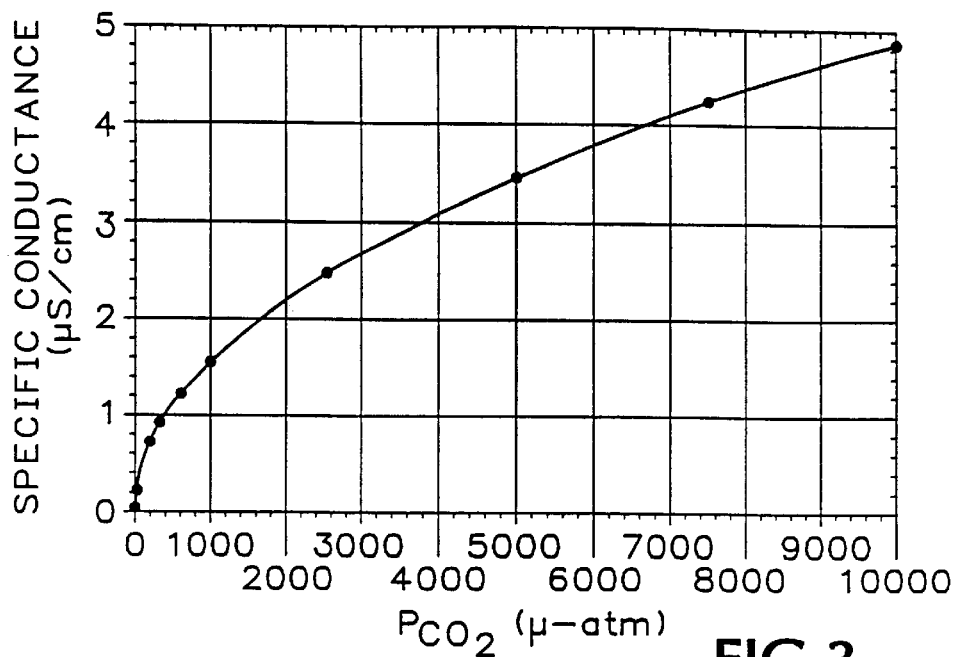
FIG. 3 is a graph showing relationship between $P_{CO_2}$ and K of deionized water at 25 degrees C.

Following equilibrium transport of dissolved or atmospheric $CO_2$ across a membrane into deionized water, the conductivity increase resulting from $CO_2$ induced ionization reactions will be proportional to the $CO_2$ concentration on the opposite side of the membrane. The relationship between $P_{CO_2}$ and K of deionized water at 25 degrees C. is illustrated in FIG. 3. The equilibrium constants $K_1$, $K_2$, corresponding to the two dissociation reactions, the Henry's Law constant $H_{CO_2}$, and the equivalent conductances ($\Lambda^\circ$) for the ionic species are all functions of temperature. Fortunately, both temperature and specific conductance can be measured very precisely using simple and reliable instruments.

The inherent weakness in using the conductivity of deionized water to monitor $CO_2$ stems from the very low levels of specific conductance which arise due to equilibration with $CO_2$. This is overcome by chemical amplification of the basic conductivity signal. Chemical amplification is achieved using aqueous chemical reagents which increase the solubility of $CO_2$ through the ionization reactions shown below. Aqueous chemical reagents such as primary and secondary alkanolamines react with dissolved $CO_2$ in a two step sequence, forming first a zwitterion, as follows:

$$R_1R_2NH + CO_2 \text{ (aq)} \overset{K_{21}}{\longleftrightarrow} R_1R_2NH^+CO_2^- \quad \text{(Eq. 1.5)}$$

which then transfers a proton to an un-ionized amine, forming the corresponding carbamate, as follows:

$$R_1R_2NH + R_1R_2NH^+CO_2^- \overset{K_{12}}{\longleftrightarrow} R_1R_2NH_2^+ + R_1R_2NCO_2^-. \quad \text{(Eq. 1.6)}$$

The reaction of tertiary alkanolamines with $CO_2$ proceeds by the formation of a protonated amine and a bicarbonate anion, $$R_1R_2R_3N + H_2O + CO_2 \text{ (aq)} \overset{K_3}{\longleftrightarrow} R_1R_2R_3NH^+ + HCO_3^-. \quad \text{(Eq. 1.7)}$$

Conductivity is enhanced by the greater equilibrium concentrations of the ionic products for these reactions as compared to those for the dissociation of $CO_2$ in pure water. Amplification is dependent on the chemical reagent employed and its concentration, the $CO_2$ concentration, contact time and the kinetic characteristics of the membrane module. For example, when 1–4 mM of monoethanolamine solution is used in an experimental module, the signal was amplified to preferably at least about 25 fold, more preferably at least about 35 fold, and most preferably at least about 50 fold.

Figure 4:
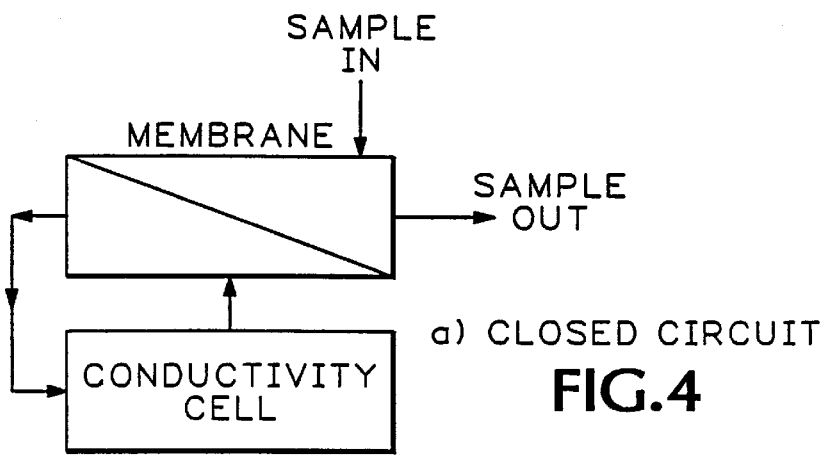
FIG. 4 is a flow schematic showing a closed circuit configuration.
Figure 5:
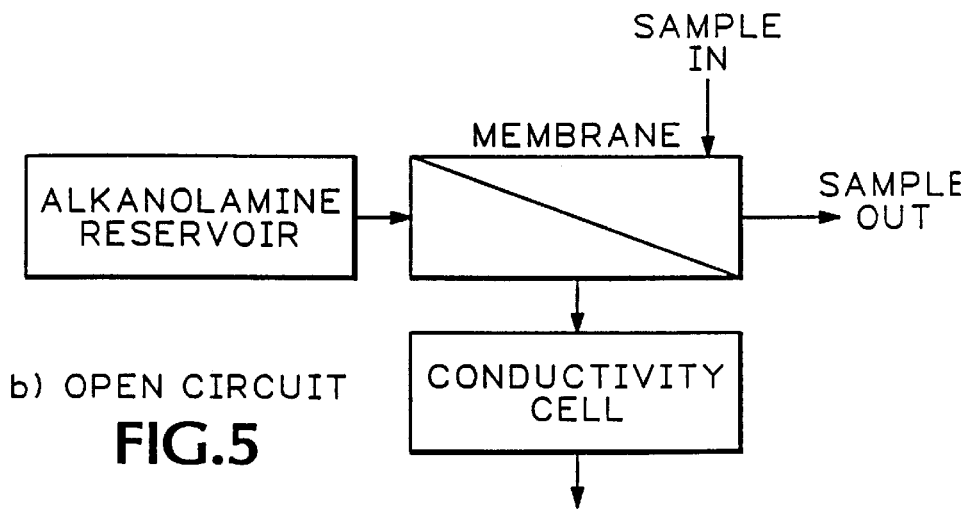
FIG. 5 is a flow schematic showing a open circuit configuration.

The three step process (membrane transport, chemical amplification, and specific conductance detection) for determining $CO_2$ levels in air and water has been evaluated in the two prime configurations illustrated schematically in FIGS. 4 and 5. These differ only in the flow characteristics of the chemical reagent solution. The Closed Circuit configuration (FIG. 4) is also represented in FIG. 1. This configuration consists of a chemical reagent solution which continuously recirculates through the conductivity cell. This represents an equilibrium detection mode in which the chemical reagent solution gains or loses $CO_2$ across the membrane in order to equilibrate with a rising or falling $P_{CO_2}$ in the surrounding air or water.

In the Open Circuit configuration (FIG. 5) the chemical reagent solution flows from a feed reservoir, first through the membrane contactor, then into the conductivity cell, and then to waste. In this configuration the expendable chemical reagent solution makes a single pass through the system. This mode of detection may or may not be an equilibrium process, depending upon the kinetics of $CO_2$ transport into the chemical reagent solution in the membrane contactor. Two Open Circuit variants, i.e., the Continuous Open Circuit variant and the Stopped Flow Injection variant, are provided. In the Continuous Open Circuit, the chemical reagent solution flows at all times.

In the Stopped Flow Injection configuration, the chemical reagent solution does not flow continuously. A volume of the chemical reagent solution is injected into the membrane contactor and then flow is stopped. After a predetermined contact time, flow is re-established. The "plug" of $CO_2$, containing chemical reagent solution is displaced from the membrane contactor, and then flows through the conductivity cell. This configuration results in a specific conductance peak which is proportional to the $P_{CO_2}$ of the surrounding air or water.

Experiments were conducted to illustrate the system and process of the present invention. As for the reagents and materials employed, a 0.976% by volume carbon dioxide in oxygen mixture was purchased from Airco Specialty Gases (Vancouver, Wash.). Two standard mixtures of carbon dioxide in air were purchased from Pacific Airgas Inc. (Portland, Oreg.). The higher concentration standard contained 750 parts per million (ppm) $CO_2$ by volume in a diluent gas consisting of 19.995% oxygen (by volume) with the balance (79.930%) consisting of nitrogen. The lower concentration standard contained 200 ppm CO2 in 20.00% oxygen and 79.998% nitrogen. Lecture bottles of 98.5% nitric oxide, and 99.9% sulfur dioxide were purchased from Aldrich (Milwaukee, Wis.).

Using the van der Waals equation of state, it was determined that errors due to non-ideality of $CO_2$ are not significant at the temperatures and pressures used herein, (i.e. 0.4% for 10,000 µatm at 25 degrees C.). Secondary standard $CO_2$ gas mixtures were prepared by pressurizing a previously evacuated gas cylinder using the 0.976% carbon dioxide in oxygen mixture, followed by subsequent pressurizations using first oxygen and then nitrogen to achieve the desired concentration of $CO_2$ in air. The oxygen and nitrogen gases used were UN1072 and UN1066 grades respectively, purchased from Oregon Airgas Inc. (Roseburg, Oreg.). Gas mixtures prepared in this way ranged in $P_{CO_2}$ between 80–600 µatm, with the remainder consisting of approximately 80% nitrogen and 20% oxygen. The values obtained by this process were verified by non-dispersive Infrared (IR) absorption measurements. Care was taken to use only $CO_2$-air mixtures owing to the documented potential for error when using nitrogen $CO_2$ mixtures in the calibration of IR cells to be used in atmospheric $CO_2$ determinations.

Two gas mixtures, containing 100 µatm Nitric Oxide (NO), and 100 µatm NO plus 200 µatm $CO_2$, respectively, were prepared by pressurizing a previously evacuated lecture bottle using 98.5% NO, followed by subsequent pressurizations using first oxygen and then nitrogen to achieve the desired concentrations in air. Analogous mixtures containing 100 µatm Sulfur Dioxide ($SO_2$),and 100 µatm SO2 plus 200 µatm CO2 were prepared. HCl mixtures were prepared from a saturated vapor enclosed in a 1L. volumetric flask. HCl vapor was removed by gas-tight syringe and used to prepare two gas mixtures within previously evacuated lecture bottles. The two mixtures consisted of 100 µatm of HCl in $CO_2$ free air, and 100 µatm of HCl plus 200 µatm $CO_2$ in air, respectively.

Synthetic seawater brine was prepared by dissolving 29.5 g reagent grade NaCl (VWR Scientific) in 970.5 g deionized water. This solution was not intended to simulate the chemical composition of true seawater, but rather to provide a suitable medium for determining instrument responses to water samples at high ionic strength.

Determinations of atmospheric $P_{CO_2}$ were performed using an Astro International Model 5600AT non-dispersive infrared absorption spectrometer with a gas-tight 13 cm path-length flow through cell. The instrument was operated in the 0–1,000 µatm carbon dioxide range. A constant sample stream flow rate of 150 $cm^3$/min was fed to the instrument by means of either a diaphragm pump or a cylinder of pressurized gas. Instrumental response time is approximately 3 seconds and repeatability is ±3% full scale or ±30 µatm $P_{CO_2}$.

The instrument was calibrated using 3 standard gases mixtures. Quadratic calibration curves were generated using the process of least squares. For on-going calculation of $P_{CO_2}$, a 40 value look-up table was created for the data logger from the calibration curve. This allowed the data logger to calculate $P_{CO_2}$ as a function of output voltage while experiments were in progress. No corrections were made for fluctuations in temperature or atmospheric pressure.

Total Inorganic Carbon (TIC) was determined using an Astro 2001 System 2 total carbon analyzer in the 0–10 mg/L range. This instrument uses acidification and sparging with IR detection. The manufacturer claims a repeatability of 0.2 mg/L for this concentration range.

Bench top specific conductance measurements were made using a Cole-Parmer model 19101-00 conductivity bridge and a Cole-Parmer model: G-01481-93 cell. In-line specific conductance measurements on flowing streams were made using Cole Parmer model MN-01481-66 flow through conductivity cells and model 19101-00 conductivity bridges. These were used as integral components of the several test stands described below. The manufacturer claims precision and accuracy for these devices of ±0.1, and ±0.2 µS/cm respectively. These instruments provided temperature compensation for the range between 5–45° C.

Closed Circuit (Recirculating) $CO_2$ Vapor Analyzer

Figure 6:
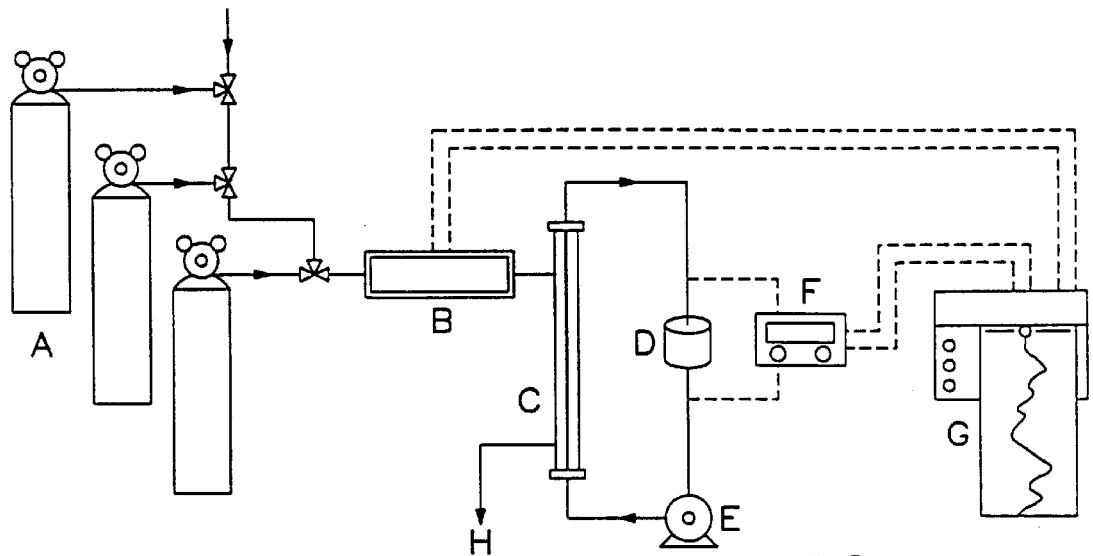
FIG. 6 is a flow schematic showing a closed circuit test apparatus used to determine atmospheric $P_{CO_2}$.

The closed circuit test apparatus used to determine atmospheric $P_{CO_2}$ is illustrated schematically in FIG. 6. The system consisted of a manifold of valve selectable calibration gas mixtures and ambient air inlet A, a membrane contactor C, a recirculating pump E(Cole Parmer model 7520-35), an in-line conductivity cell D and bridge F, a non-dispersive IR cell B, and a data logger G(Molytek model 3702). Separate membrane contactors C, including a vent H to the atmosphere, were prepared from each of the three polymers: PTFE, Siloxane, and microporous polyypropylene (uPP). The Siloxane gas-liquid membrane contactor consisted of a single 1524 cm length of fiber (0.031 cm ID×0.064 cm OD) in a glass shell with an internal liquid volume of 1.1 $cm^3$, an external gas volume of 1000 $cm^3$, and a membrane gas-liquid contacting surface area of 146 $cm^2$. The PTFE gas-liquid membrane contactor consisted of a single 2438 cm fiber (0.051 cm ID×0.061 cm OD) in a glass shell with an internal liquid volume of 5.0 $cm^3$, an external gas volume of 1000 $cm^3$, and a membrane gas-liquid contacting surface area of 391 $cm^2$. The uPP'gas-liquid membrane contactor consisted of a single 610 cm fiber (0.040 cm ID×0.046 cm OD) in a polyethylene shell with an internal liquid volume of 0.8 $cm^3$, an external gas volume of 12.1 $cm^3$, and a membrane gas-liquid contacting surface area of 24.4 $cm^2$.

Closed Circuit (Recirculating) $CO_2$ Detection

Atmospheric detection experiments were conducted using the apparatus described in FIG. 6. Standard compressed $CO_2$-air mixtures or ambient laboratory atmosphere samples were fed to the shell side of the gas-liquid membrane contactor at 150 cM$^3$/min after flowing through the IR cell. A 0.001M solution of aqueous DEA was recirculated through the inner volume of the hollow fiber membranes and then through an in-line conductivity cell. Specific conductances, ambient temperatures, IR derived $P_{CO_2}$ values, and elapsed times were recorded on disk by means of the data logger.

Open Circuit (Single Pass) $CO_2$ Vapor Analyzer

Figure 7:
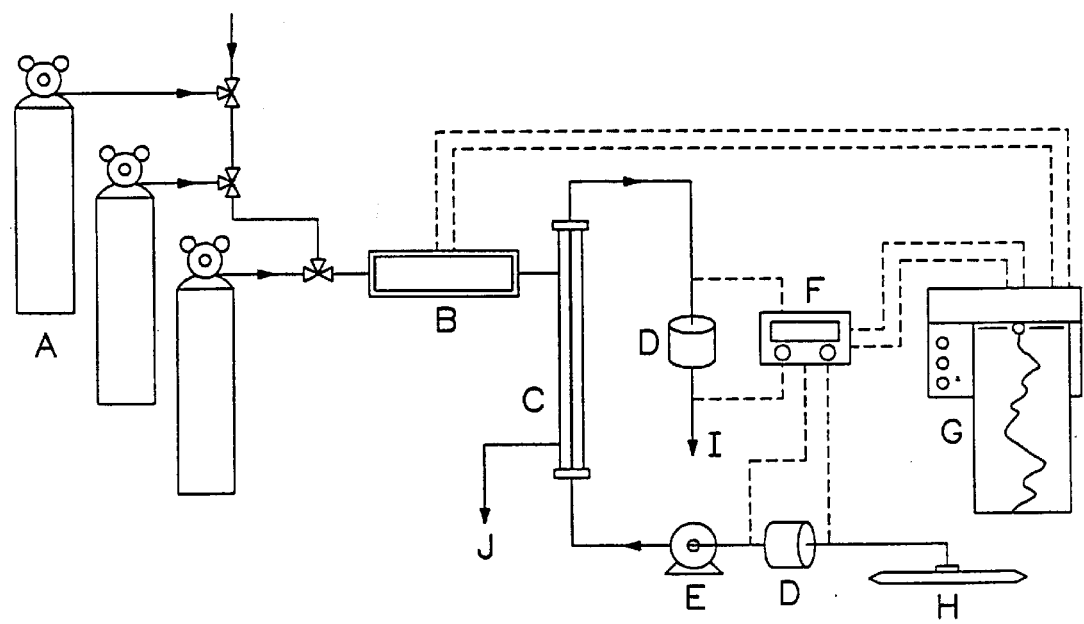
FIG. 7 is a flow schematic showing an open circuit test apparatus used to determine atmospheric $P_{CO_2}$.

The open circuit test apparatus used to determine atmospheric $P_{CO_2}$ is illustrated schematically in FIG. 7. The system consisted of a manifold of valve selectable calibration gas mixtures and ambient air inlet A, a membrane contactor C, a chemical reagent pump E (Cole Parmer model 7520-35), a zero headspace Tedlar chemical reagent feed reservoir H (Jensen Inert Products, Miami, Fla.), a feed conductivity cell D1 and bridge F, with an outlet to liquid waste I, an in-line conductivity cell D2 and bridge I2, a non-dispersive IR cell B, and a data logger G (Molytek model 3702). In this configuration, specific conductance was determined as the differential between the properties of influent and effluent chemical reagent. Two gas-liquid contactor modules were used in this test configuration. A $\mu$PP membrane contactor was prepared using a single 90 cm long fiber (0.040 cm ID×0.046 cm OD) in a glass shell. This module had an internal liquid volume of 0.1 cm$^3$, an external gas volume of 1000 cm$^3$ and a membrane gas-liquid contact area of 11.3 cm$^2$. The second module used was the PTFE module described above.

Apparatus for Equilibration of Seawater with $CO_2$

This apparatus was used as a means of preparation of synthetic seawater samples which were equilibrated with known atmospheric $P_{CO_2}$ levels. The synthetic seawater brines were then used as influent samples for challenge of the Open Circuit Seawater $CO_2$ Analyzer.

Figure 8:
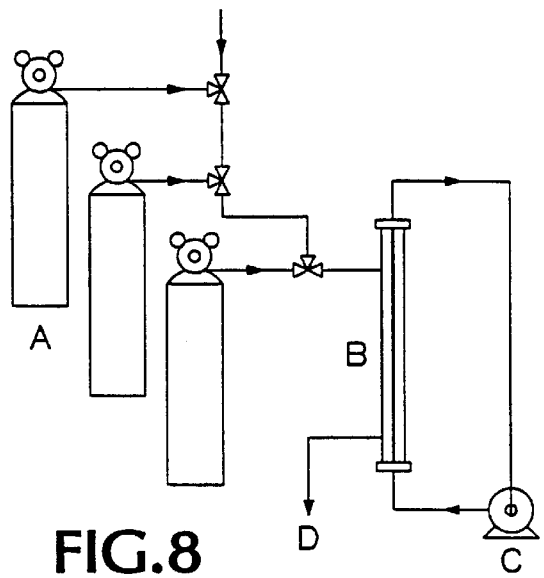
FIG. 8 is a flow schematic showing an apparatus for equilibration of synthetic seawater with atmospheric $P_{CO_2}$ levels.

The apparatus, illustrated schematically in FIG. 8, consisted of a manifold of valve selectable calibration gas mixtures and ambient air inlet A, a gas-liquid membrane contactor B with a vent to the atmosphere D, and a brine recirculation pump C (Cole Parmer model 7520-35). The hollow fiber membrane contactor was constructed using a bundle of 36 $\mu$PP fibers in a polycarbonate shell. Each fiber was 22 cm long (0.040 cm ID×0.046 cm OD). The contactor internal liquid volume was 1.0 cm$^3$, with an external gas volume of 95 cm$^3$ and a membrane surface area of 100 cm$^2$. The high surface to volume ratio in the contactor ensured rapid equilibration compared to other gas-liquid exchange process.

In operation, the shell side of the apparatus was fed either ambient laboratory atmosphere or compressed gas mixtures at a flow rate of 150 cm$^3$/min. The influent to the apparatus was most commonly the effluent gas from the IR cell. The tube side of the membrane contactor was initially charged with synthetic seawater, described above, by means of a peristaltic pump from a 4 L reservoir. Once charged, the synthetic seawater recirculated through the interior of the contactor for equilibration with the gas phase in accordance with Henry's Law.

Open Circuit (Single Pass) Seawater $CO_2$ Analyzer

Figure 9:
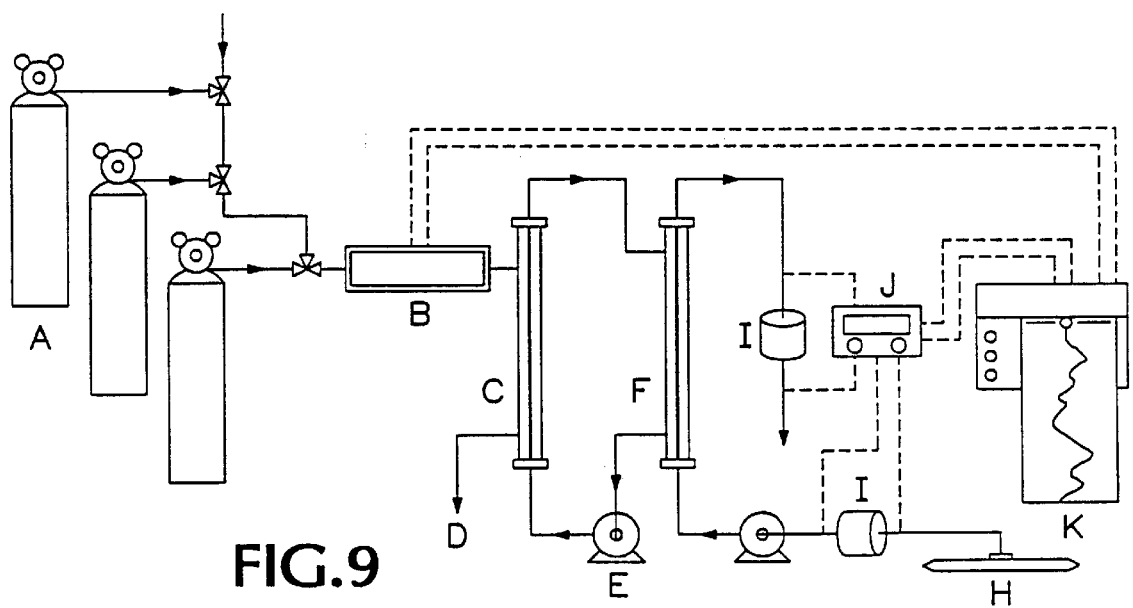
FIG. 9 is a flow schematic showing an open circuit test apparatus used to determine $P_{CO_2}$ in synthetic seawater.

The open circuit test apparatus used to determine $P_{CO_2}$ in synthetic seawater is illustrated schematically in FIG. 9. The apparatus consisted of a manifold of valve selectable calibration gas mixtures A, a liquid-liquid membrane contactor F, an chemical reagent pump G (Cole Parmer model 7520-35), a zero headspace Tedlar chemical reagent feed reservoir H, a feed conductivity cell I1 and bridge I1, an in-line conductivity cell J1 and bridge J2, a non-dispersive IR cell B, and a data logger K (Molytek model 3702). In this configuration, specific conductance was determined as the differential between the conductivities of influent and effluent chemical reagents. Additionally, the apparatus consisted of the seawater $CO_2$ equilibrator previously discussed, including gas/liquid membrane contactor C with vent to atmosphere D, and brine recirculator pump E. The liquid-liquid membrane contactor was fabricated using a single 610 cm length of $\mu$PP in a fluorinated ethylene propylene (FEP) shell. The internal chemical reagent volume was 0.8 cm$^3$, with an external synthetic seawater volume of 11.0 cm$^3$, and a liquid-liquid contact area of 78 cm$^2$. In operation, the brine recirculated through both a gas-liquid and a liquid-liquid membrane contactors, C and F. The first contactor was a device for producing the desired synthetic seawater $P_{CO_2}$. The liquid-liquid contactor transported $CO_2$ from the brine to the chemical reagent solution, and was the fundamental step required for the quantitative analysis.

Fully Integrated Test Apparatus

Figure 10:
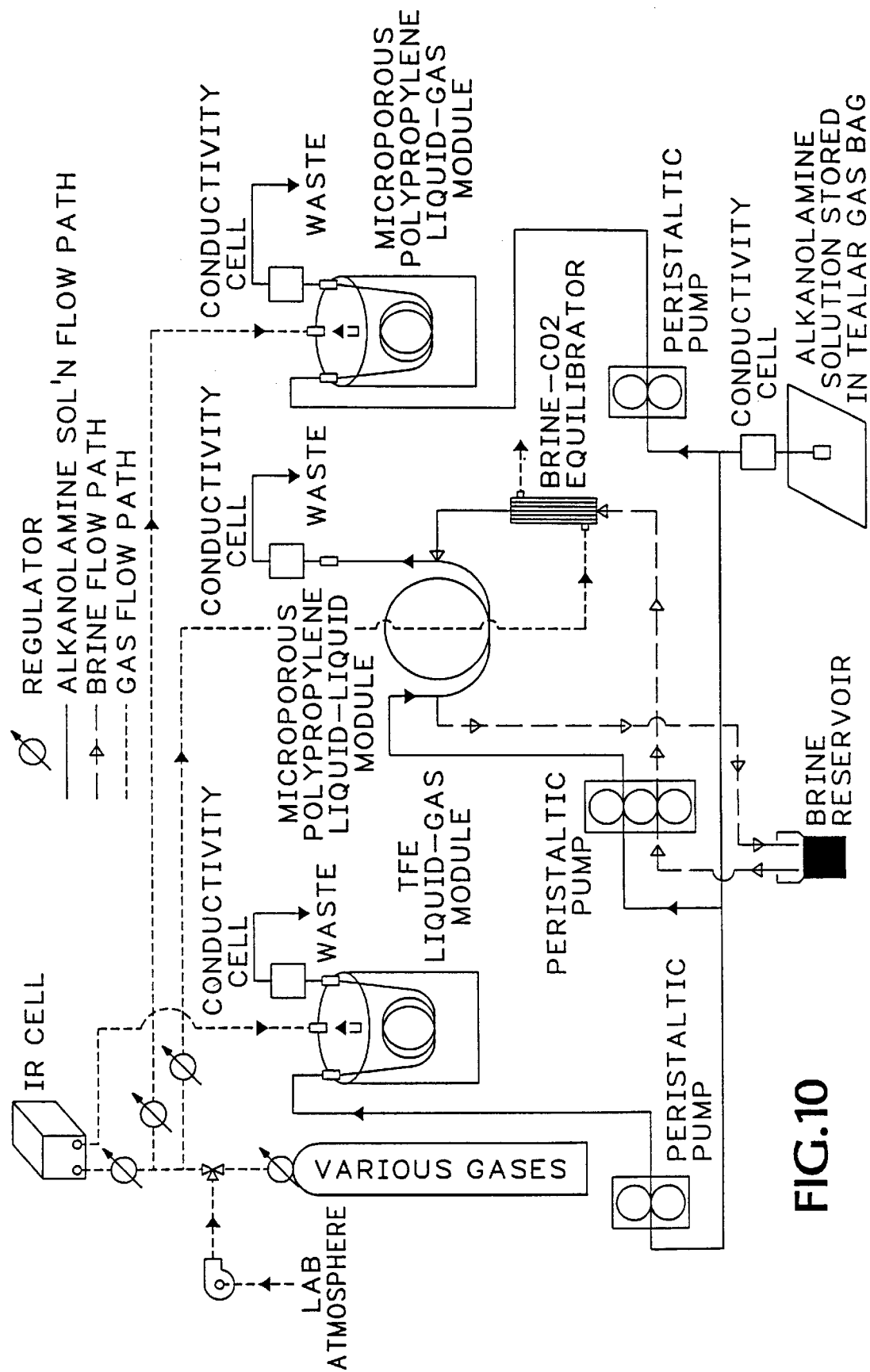
FIG. 10 is a flow schematic showing an integrated oceanic $CO_2$ sensor test stand.

To facilitate the performance of several experiments simultaneously, the $CO_2$ analyzer configurations illustrated in FIGS. 7 and 9 were integrated into a single Open Circuit Operational Test Stand (FIG. 10). The integrated apparatus incorporated three membrane contactors: the gas-liquid PTFE and RPP modules and the liquid-liquid $\mu$PP module. The integrated apparatus was used for the determination of both atmospheric and seawater $P_{CO_2}$.

Stopped Flow Injection Seawater $CO_2$ Analyzer

Figure 11A:
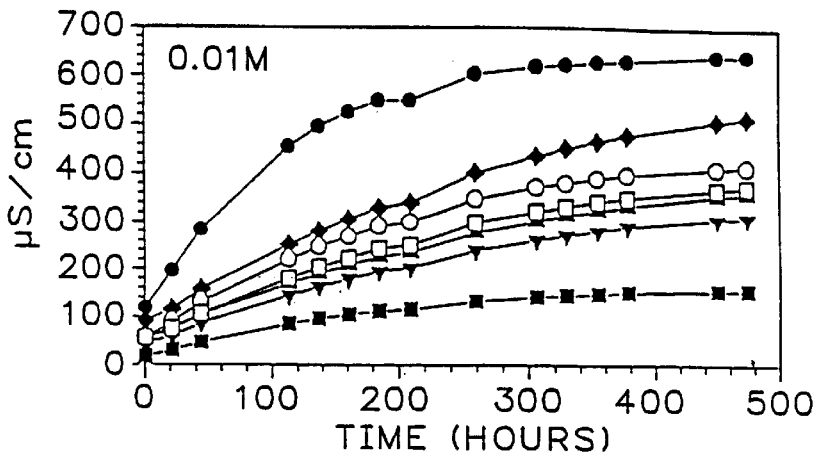
FIGS. 11A–11C are graphs showing sorption of atmospheric $CO_2$ by various chemical reagent solutions.
Figure 11B:
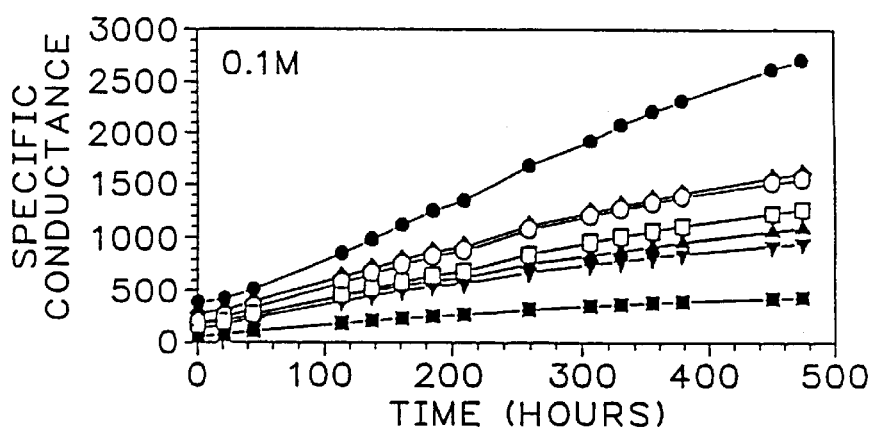
Figure 11C:
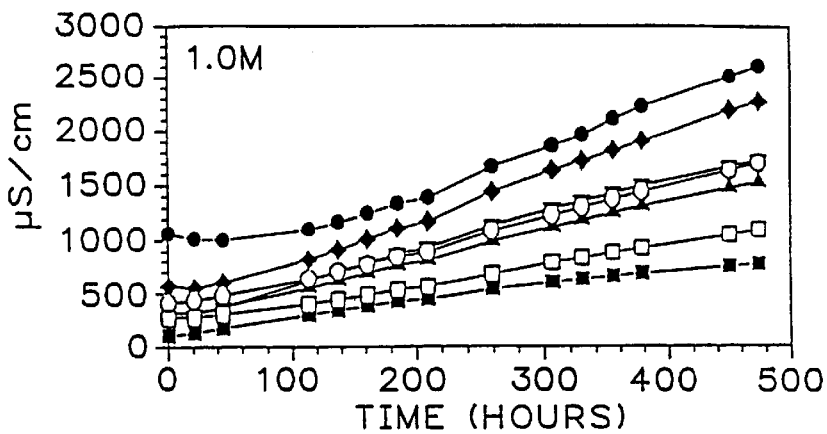

The apparatus used for the stopped flow chemical reagent injection determinations of $P_{CO_2}$ in synthetic seawater is illustrated schematically in FIG. 11. The system consisted of chemical reagent feed reservoir A, a hollow fiber liquid-liquid membrane contactor E, an chemical reagent feed peristaltic pump B (Cole Parmer model 755360), a brine standard/sample reservoir C, a brine feed peristaltic pump D (Cole Parmer), a conductivity cell F, and strip chart recorder G (Omega model 585-11-13). The liquid-liquid exchange module was fabricated using a 305 cm length of $\mu$PP, inside a non-permeable FEP shell. This configuration yielded a shell side (synthetic $P_{CO_2}$ standard) volume of 57 cm$^3$, a tube side internal volume of 0.277 cm$^3$, and a total membrane surface area of 33 cm$^3$.

$CO_2$ Absorption

An experiment was conducted to compare the relative rates of $CO_2$ uptake as a function of concentration for a variety of chemical reagents. 1.0, 0.1, and 0.01 M solutions of seven alkanolamines, diethanolamine (DEA), monoethanolamine (MEA), triethanolamine, N,N-dimethylethanolamine, N-methylethanolamine, N-ethylethanolamine, and Diisopropanolaminewere prepared in deionized water. 100 mL of each solution was then transferred to a 125 mL unstoppered wide mouth bottle. The alkanolamine solutions were exposed to the changing $CO_2$ concentrations of the ambient laboratory atmosphere for a period of approximately 500 hours. Specific conductances of the solutions and TIC were periodically monitored and recorded.

$CO_2$ Absorption Reversibility

To achieve a viable technique for $CO_2$ determination in the Closed Circuit (recirculating) configuration, the sorption of $CO_2$ by the chemical reagent solution must be reversible. To test the relative reversibility trends of $CO_2$ sorption for several of chemical reagents, in the form of 0.001 M alkanolamine solutions, were saturated with $CO_2$ and then sparged with $N_2$. The change in alkanolamine-$CO_2$ concentration was determined by monitoring specific conductance and TIC. 80 mL aliquots of deionized water and 0.001M aqueous solutions of ethanolamine (MEA), diethanolamine (DEA) and diisopropanolamine (DIPA) were transferred to 100 mL beakers. Initial conductivity and TIC was determined. The solutions were then sparged with a humidified 1% $CO_2$ in oxygen gas mixture at a flow rate of 150 $cm^3/min$, for a period of twenty minutes. Conductivity and TIC were measured again. The solutions were then passively exposed to the ambient laboratory atmosphere overnight. The samples were then subjected to a humidified nitrogen sparge at a flow rate of 150 $cm^3/min$ for a period of 19 hours. Specific conductance measurements were made after 1, 2, and 19 hours of sparging.

Open Circuit $CO_2$ Detection In Seawater

Open circuit atmospheric $CO_2$ detection experiments were conducted using the apparatus described above. Standard compressed $CO_2$-air mixtures or ambient laboratory atmosphere samples were fed to the shell side of the gas-liquid membrane contactor at 150 $cm^3/min$ after flowing through the IR cell. A 0.001M solution of aqueous MEA was pumped from a zero headspace Tedlar gas bag feed reservoir, through an in-line conductivity cell, into the hollow fibers within the membrane gas-liquid contactors, and then through a second in-line conductivity cell. In this configuration differential specific conductances were monitored using the difference in value between influent and effluent specific conductance measurements. Differential specific conductances, ambient temperatures, IR derived $PCO_2$ values, and elapsed times were recorded on disk by means of the datalogger.

Open Circuit Atmospheric $O_2$ Detection

Open circuit detection experiments for monitoring $CO_2$ in seawater were conducted using the apparatus described above. Samples of synthetic seawater containing known $P_{CO_2}$ values were obtained by membrane equilibration using the system delineated above. Standard compressed $CO_2$-air mixtures or ambient laboratory atmospheric samples were fed to the shell side of the gas-liquid membrane contactor at 150 $cm^3/min$ after flowing through the IR cell. Synthetic seawater was recirculated through the lumen of the gas-liquid membrane contactor at a flow rate of 3 $cm^3/min$. TIC levels in the recirculating synthetic seawater indicated equilibrium exchange.

The $CO_2$ equilibrated brine was fed into the shell side of the liquid-liquid membrane contactor. A 0.001M solution of aqueous MEA was pumped from a zero headspace Tedlar gas bag feed reservoir, through an in-line conductivity cell, into the lumen of the hollow fiber membrane liquid-liquid contactor, and then through a second in-line conductivity cell. The effluent from the second conductivity cell was routed to the waste container. In this configuration differential specific conductances were monitored using the difference in value between influent and effluent specific conductance measurements. Differential specific conductances, ambient temperatures, IR derived $PCO_2$ values, and elapsed times were recorded on disk by means of the data logger.

Stopped Flow Alkanolamine Injection $CO_2$ Detection

Synthetic standards with constant $P_{CO_2}$ were prepared by buffering both pH and $P_{CO_2}$ in a 0.01M $NaHCO_3$ - 0.05 M borate buffer solution. The $P_{CO_2}$ values for these solutions were calculated from the pH, the first and second dissociation constants for carbonic acid ($K_1$ and $K_2$ defined in equations 1.2 and 1.3), Henry's Law constant ($H_{CO_2}$), and the total carbonate species concentration ($C_T$) as in Equation 2.1, $$C_T = [CO_3^=] + [HCO_3^-] + [CO_2] \quad \text{(Eq. 2.1)}.$$

For calculation of $PCO_2$ it was assumed that the sum of all carbonate species was equal to the $HCO_3$- concentration. This assumption is valid for the pHs used to buffer this system. The impact on $C_T$ ($\cong$0.01 M $HCO_3$-) of 200–750 $\mu$atm (0.278 to 1.04 mg/L $CO_2$) is insignificant. Also, a small volume of 0.001 M MEA solution across a liquid-liquid membrane contactor, does not have the capacity to scavenge sufficient $CO_2$ from this solution to change its concentration. The 0.05 M borate buffer is also little affected by changes in the dissolved $CO_2$, and as a result, the equivalent inorganic carbon speciation and $P_{CO_2}$ in the buffered brine solution is described by the system identified in Equations 2.2–2.5.

$$[CO_2] = \frac{[HCO_3^-][H^+]}{K_1} \quad \text{(Eq. 2.2)}$$

$$[HCO_3^-] = \frac{C_T[H^+]}{K_2 + [H^+]} \quad \text{(Eq. 2.3)}$$

$$[CO_2] = \frac{C_T[H^+]^2}{K_1 K_2 + K_1[H^+]} \quad \text{(Eq. 2.4)}$$

$$P_{CO_2} = \frac{C_T[H^+]^2}{H_{CO_2} K_1 K_2 + K_1[H^+]} \quad \text{(Eq. 2.5)}$$

The pHs of three different 0.01M $NaHCO_3$- 0.05 M borate buffer solutions were adjusted to give $P_{CO_2}$ values of 256, 544, and 745 $\mu$atm. Although these $CO_2$ values are not compensated for solution non-ideality and consequently are accurate to only two significant figures, they are constant for each buffer solution and their use in generation of statistical deviations is valid.

The stopped flow chemical reagent injection liquid phase $CO_2$ detection experiments were conducted using the apparatus described above. The shell side of the liquid-liquid membrane contactor was filled with $P_{CO_2}$ buffer solutions. An aqueous 0.001 M MEA solution was pumped into the lumen of the liquid-liquid membrane contactor at a flow rate of 0.56 $cm^3/min$. The flow was then stopped for a specified contact period. These experiments were conducted using contact times of 5, 10, 15, 20, 30, and 50 minutes. At the end of the contact time period, the chemical reagent solution was pumped through the in-line conductivity cell, and the corresponding conductivity peak recorded. Characterization of Temperature Effects.

A liquid-liquid membrane contactor was constructed consisting of a single $\mu$PP 305 cm fiber inside an impermeable FEP shell of equal length. This configuration yielded an internal liquid volume of 0.4 $cm^3$ and an external shell side liquid volume of 5.6 $cm^3$, with a 32 $cm^2$ membrane surface area. The membrane contactor was integrated into an open circuit apparatus similar to that described above, but housed inside a commercially available 48 quart ice chest, filled with 8±1° C. water, fitted with thermal equilibration coils, and instrumented with a K- type thermocouple.

Synthetic seawater was equilibrated with gases of varying $CO_2$ content using the apparatus previously described. The sample was then circulated through first a 150 cm thermal equilibration coil, and then the shell side of the membrane contactor located within the cooler. A 0.001M MEA solution was pumped from the gas tight reservoir at room temperature, through the first in-line conductivity cell, then through the 150 cm thermal equilibration coil, through the lumen of the hollow fiber membrane contactor, and into a temperature compensated conductivity cell co-located within the cooler, just above the water line.

Elevated temperature measurements were obtained in a similar manner using the apparatus with an internal water bath temperature of 30±1° C. Room temperature measurements were obtained at 21±1° C.

Interferences

The $\mu$PP membrane contactor and open circuit gas-liquid $CO_2$ detection apparatus described above were used to determine the interference effects of HCl, NO, and $SO_2$ on the specific conductance of chemical reagent solutions. The apparatus was operated in the normal $CO_2$ detection mode. For these experiments the apparatus was installed inside a fume hood. Similar experiments were performed using each of the acid gases.

The apparatus was first exposed to 200 $\mu$atm $CO_2$ in air until a steady output conductivity signal was achieved. Next, the apparatus was challenged with a gas mixture containing 100 $\mu$atm of the subject acid gas plus 200 $CO_2$ in air. This was followed by exposure to a nitrogen-oxygen mixture, free of both the subject acid gas and $CO_2$, until a stable conductivity signal was again achieved. Lastly a mixture containing 100 $\mu$atm of the subject acid gas in $CO_2$ free air was sampled. The differential specific conductances under each of these conditions were recorded.

Solid Phase Calibration Experiments

A liquid-liquid contactor was fabricated consisting of one 762 cm $\mu$PP tube inside an FEP shell of equal length. Internal volume and surface area for the hollow fiber were 0.7 $cm^3$ and 96 $cm^2$ respectively. External shell side volume was 55 $cm^3$. A packed bed containing 5 $cm^3$ of a crystalline calcium carbonate based solid phase basification material (manufactured by Umpqua Research Company) was prepared inside a 0.64 cm OD FEP tube. A similar bed was prepared from a crystalline molybdenum trioxide based solid phase acidification material (manufactured by Umpqua Research Company). These two components were plumbed in series. Using a peristaltic pump, degassed deionized water was pumped, from a gas tight reservoir, through the calcium carbonate bed for the controlled dissolution of inorganic carbon, and then through the molybdenum trioxide bed for acidification of the stream. The effluent from the acidification module was then routed through the lumen of the hollow fiber liquid-liquid contactor. 0.001 M MEA was pumped by a peristaltic pump from a gas tight reservoir through an influent conductivity measuring cell, into the external shell of the membrane contactor, through a conductivity cell, and finally to an effluent collection reservoir. Differential specific conductance, pH and TIC were measured.

EXAMPLE 1

The sorption of atmospheric $CO_2$ by chemical reagent solutions was determined. This was done by measuring the $CO_2$ absorptive properties of seven alkanolamines. The alkanolamines included primary, secondary, and tertiary alkanolamines, bearing two and three carbon alkanol groups, and ethanolamines bearing methyl, dimethyl, and ethyl alkyl groups. Results of the $CO_2$ absorption tests, using these substances at concentrations spanning a three decade range between 1.0 and 0.01 M, are given graphically in FIGS. 11A–11C. Similar results were shown for these alkanolamines with respect to concentration. Higher molarities of alkanolamine result in higher specific conductances at $CO_2$ saturation. Ethanolamine, N,N-dimethyl ethanolamine, and diethanolamine are the most preferred species for translating $CO_2$ sorption into a specific conductance signal.

For the purposes of incorporation into an analytical instrument, favorable time response characteristics are as important as strength of the primary measurement signal. These $CO_2$ sorption experiments highlight the benefit of lower chemical reagent concentrations for an application in which the fastest achievable response characteristics are desired.

EXAMPLE 2

Figure 12:
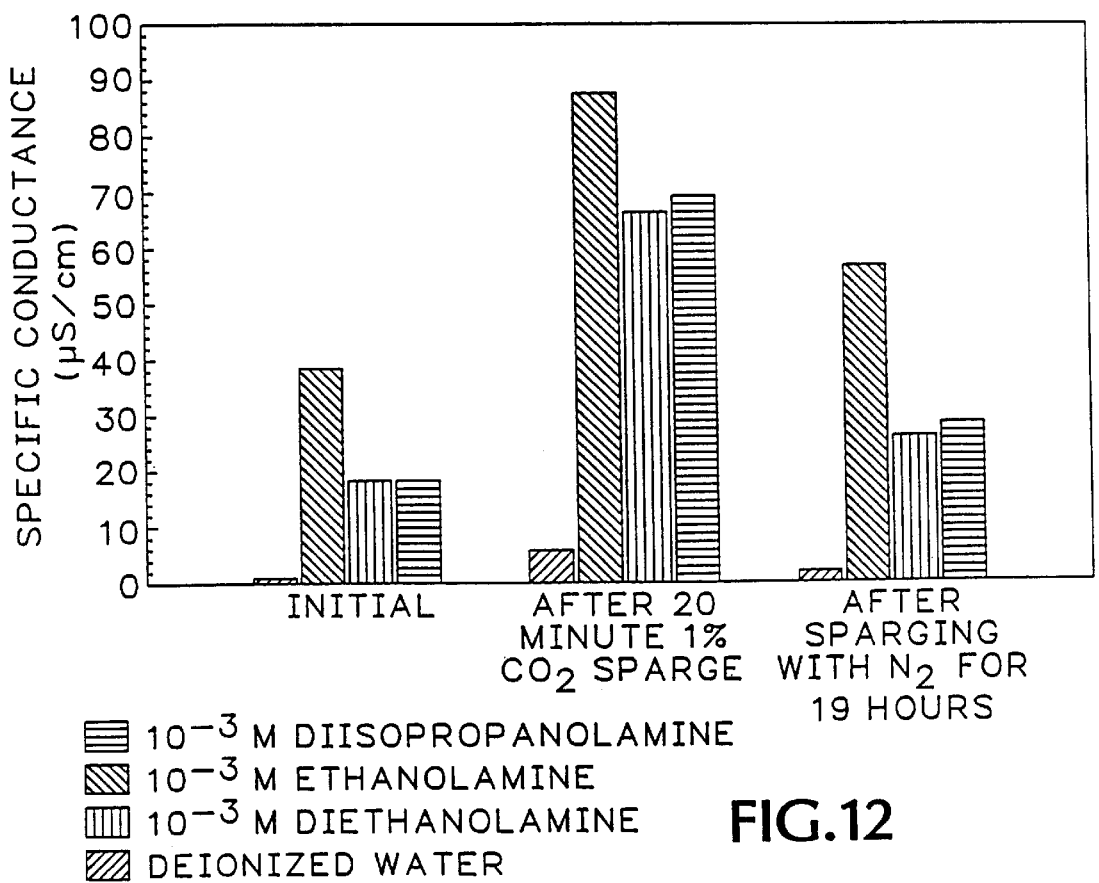
FIG. 12 is a graph showing three alkanolamines (MEA, DEA, and DIPA) that were screened for reversibility characteristics.

For operation of the $CO_2$ sensor by equilibration of an chemical reagent solution with a gaseous or dissolved $CO_2$ sample, the absorption must be reversible, and the kinetics of desorption must be sufficiently rapid to achieve an acceptable detector time response. Three alkanolamines, (MEA, DEA, and DIPA) were screened for reversibility characteristics. The experimental results are presented graphically in FIG. 12. Testing was conducted using the tube within a tube configuration, consisting of a single hollow fiber membrane strand located inside a length of larger impermeable tubing. Hollow fiber bundles were used for saturation of synthetic seawater with $CO_2$. The first sensor configuration examined was the recirculating chemical reagent closed circuit.

Figure 13:
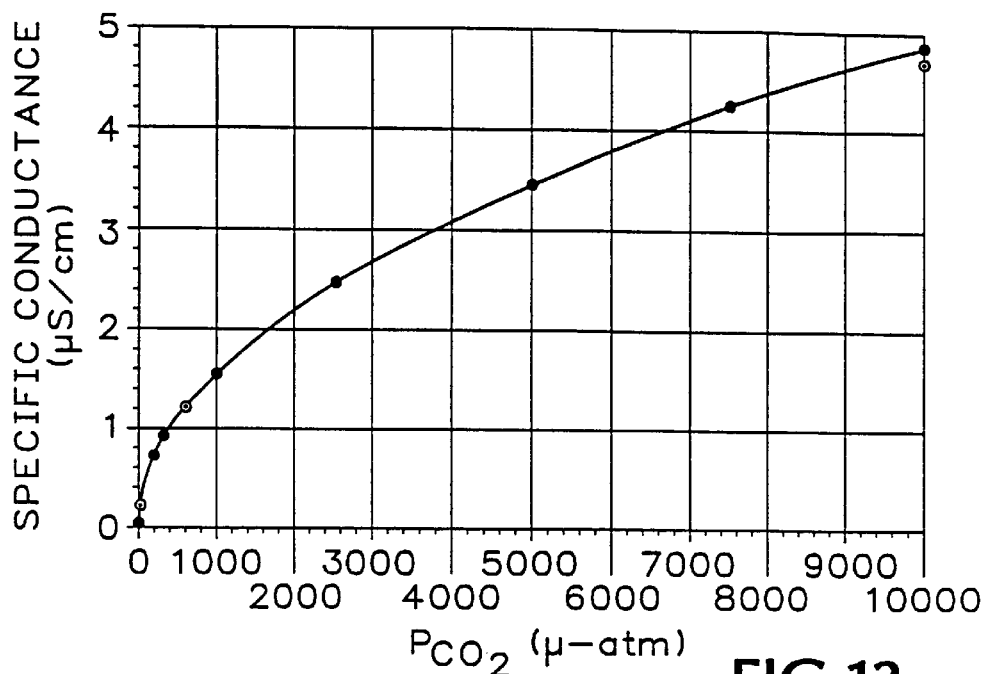
FIG. 13 is a graph showing the behavior of a recirculating deionized water loop when exposed to varying levels of atmospheric $CO_2$ ranging between 0–10,000 $\mu$atm.

Prior to experimentation with chemical reagents, the behavior of a recirculating deionized water loop was characterized when exposed to varying levels of atmospheric $CO_2$ ranging between 0–10,000 $\mu$atm. A microporous polypropylene membrane was used. As shown in FIG. 13, the experimental results correspond to theoretical values predicted by Henry's Law, the $CO_2$ dissociation equilibria, and equivalent conductances at infinite dilution for H+, OH–, $HCO_3$–, and $CO_3$=. This confirmed the operability of the experimental apparatus.

EXAMPLE 3

Figure 14:
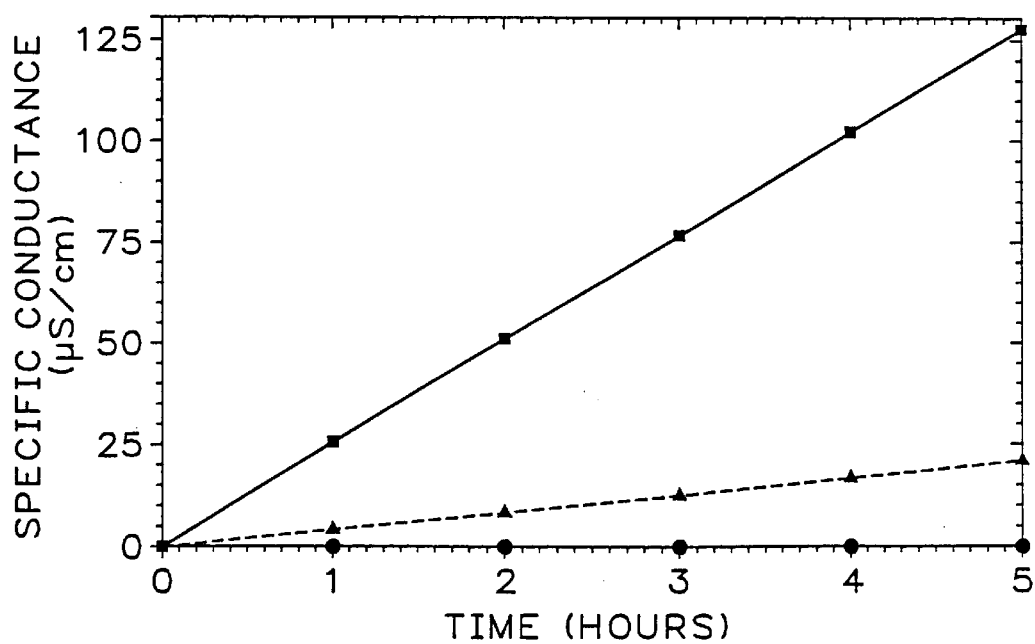
FIG. 14 is a graph showing closed circuit atmospheric $CO_2$ tracking experiments.

Closed circuit atmospheric $CO_2$ tracking experiments were conducted using the apparatus illustrated in FIG. 6, 0.001M DEA solutions, and gas-liquid contactors utilizing non-porous polydimethylsiloxane, non-porous polytetrafluoroethylene, and microporous polypropylene membranes. Each $CO_2$ detection circuit was exposed to the ambient laboratory atmosphere and the change in conductivity versus time was monitored. In all cases a continuously increasing conductivity baseline was observed due to transport of water vapor across the semipermeable membranes into the gaseous phase. This resulted in a net concentration of the DEA solution with a corresponding increase in baseline specific conductances. As illustrated in FIG. 14, the relative susceptibilities of the three membranes to water loss follows the relation Siloxane >>$\mu$PP>PTFE. The rates of baseline elevation for both the Siloxane and $\mu$PP membranes were sufficiently large that no useful $CO_2$ tracking data was obtained.

The rates of water loss across the PTFE membrane were sufficiently slow as to allow a reasonably accurate quantitative tracking of changing $CO_2$ concentrations. This was achieved by baseline compensation using a linear equation, and calibration of the closed circuit $CO_2$ sensor by comparison of IR derived $CO_2$ values and sensor derived specific conductances. The raw data, baseline corrected data, and $P_{CO_2}$ vs time in comparison to IR are shown in FIGS. 15A–15C, respectively.

In this tracking experiment, the Closed Circuit $CO_2$ Vapor Sensor was operated continuously for a period of approximately 60 hours. Changing $P_{CO_2}$ levels were tracked over this time period using the IR cell. The conductivity versus time traces of FIGS. 15A–15B, and the $P_{CO_2}$ versus time trace of FIG. 15C, indicate cyclic fluctuations in atmospheric $P_{CO_2}$, with a 24 hour periodicity. Each of these maxima correspond to levels of peak daytime activity within the laboratory and reflect maximum $P_{CO_2}$ values in the range between 480–490 $\mu$atm. Periods of minimum $P_{CO_2}$ correspond to evenings and nights. At these times $P_{CO_2}$ within the laboratory fell to values between 380–400 $\mu$atm.

Figure 15A:
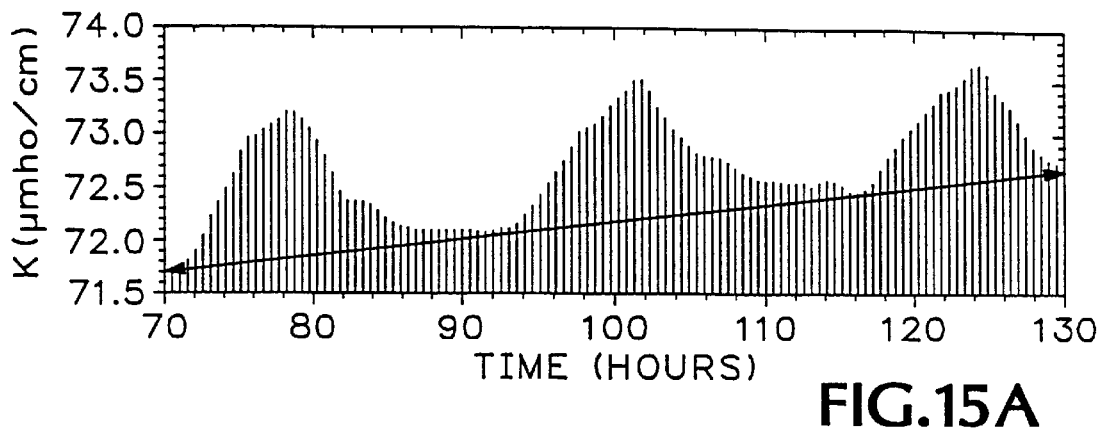
FIGS. 15A–15C are graphs showing raw data, baseline corrected data, and $P_{CO_2}$ vs time in comparison to IR.
Figure 15B:
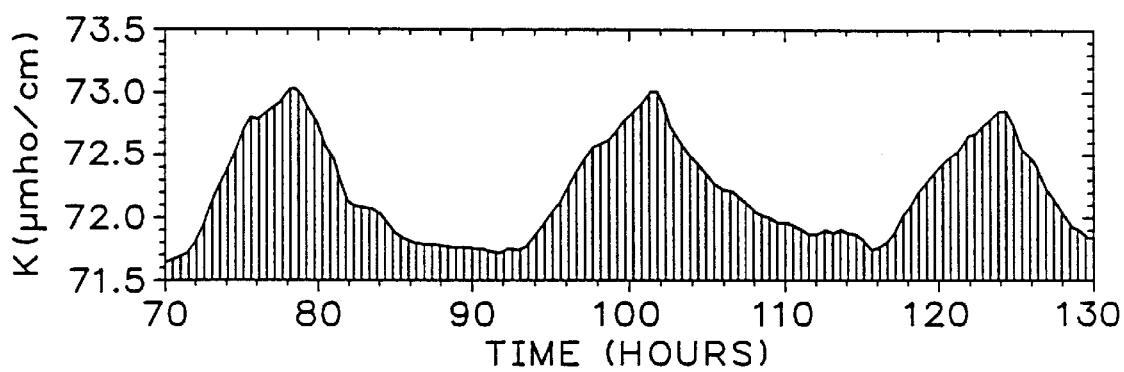
Figure 15C:
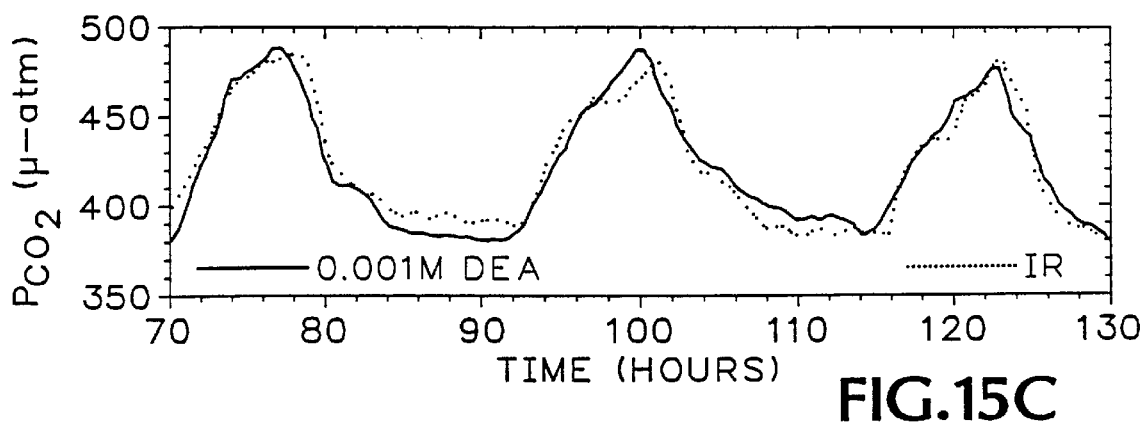
Figure 16:
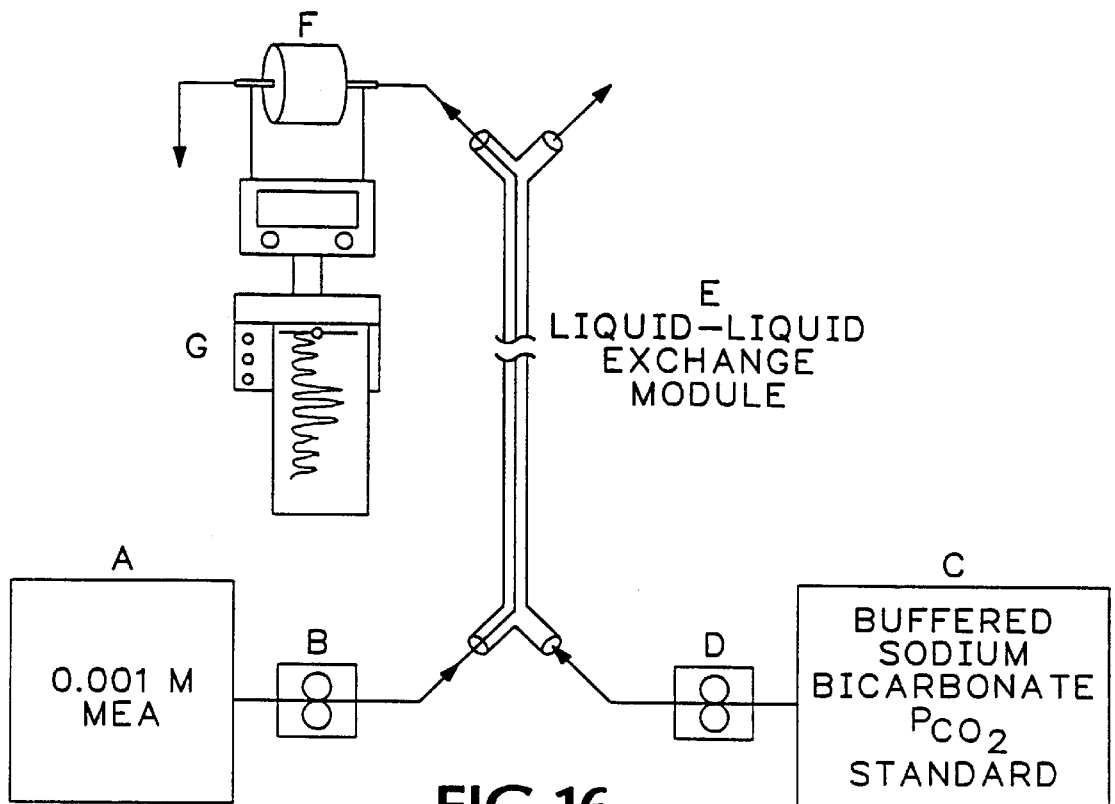
FIG. 16 is a flow schematic showing stopped flow chemical reagent injection determinations of $P_{CO_2}$ in sea water.

Inspection of FIGS. 15A–15C clearly indicate that the Closed Circuit $CO_2$ Vapor Sensor faithfully tracked the relative fluctuations of the laboratory atmospheric $P_{CO_2}$ over the full time course of this experiment. As shown in the cross-plot of IR derived $P_{CO_2}$ versus Vapor Sensor $P_{CO_2}$ given in FIG. 16, the two agreed to within ±5%. This level of accuracy was obtained under circumstances in which the deviation in specific conductance between $P_{CO_2}$ maxima and minima was less than 1.5 $\mu$S/cm. Given the non-optimized configuration of the sensor used in this experiment, the results are taken as strong indication of the potential of this process for precise long term quantitative determination of atmospheric $P_{CO_2}$.

EXAMPLE 4

Open circuit atmospheric $CO_2$ detection was conducted, as described in Example 4, using a $\mu$PP membrane contactor and an open circuit atmospheric $CO_2$ detection configuration, similar to that illustrated in FIG. 7, but with only a single in-line conductivity cell. In this configuration, 0.001 M MEA was used for chemical amplification. In the open circuit configuration the chemical reagent solution does not recirculate. Instead, it flows through the membrane contactor into the conductivity cell, and then to waste. For this reason, reversibility of the $CO_2$ absorption is not important, and hence the more active but less readily reversible MEA was used.

Figure 17A:
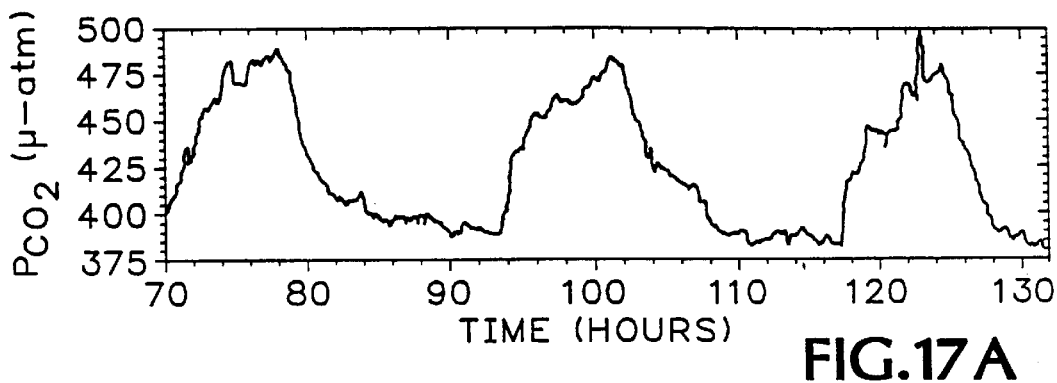
FIGS. 17A–17C are graphs showing IR derived $P_{CO_2}$, baseline compensated detector response, and raw response data respectively.
Figure 17B:
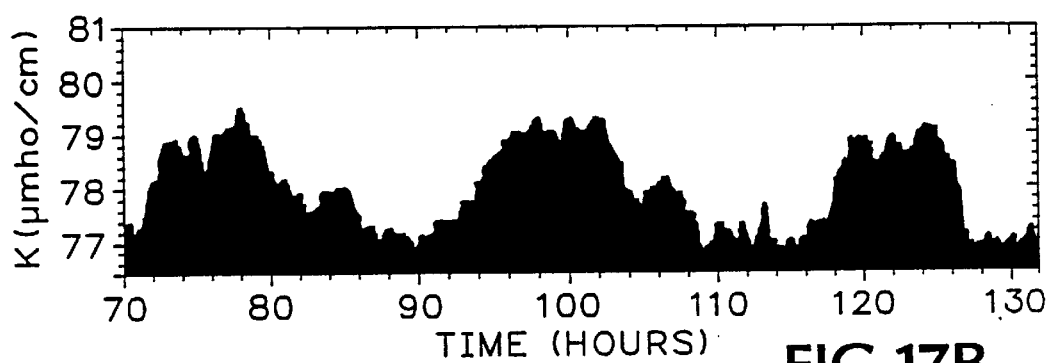
Figure 17C:
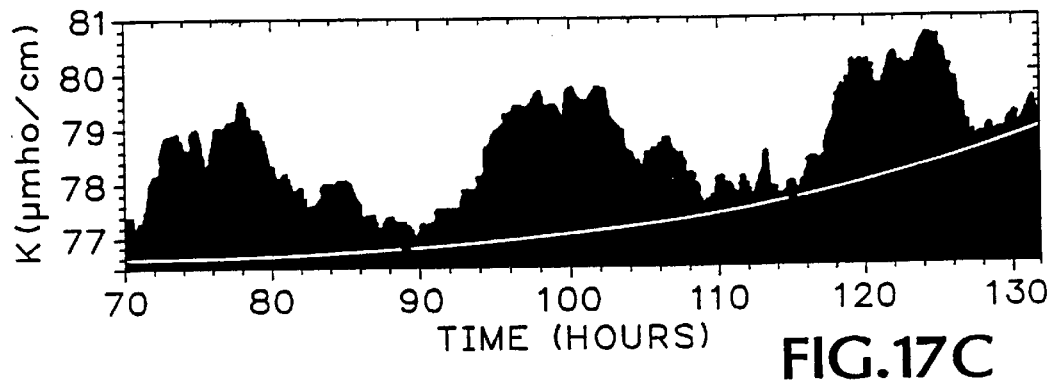

The open circuit atmospheric $CO_2$ tracking results are shown graphically in FIG. 17. FIGS. 17A–17C present IR derived $P_{CO_2}$, baseline compensated detector response, and raw response data respectively. Inspection of FIG. 17C indicates a curvilinear rising baseline. This was due to absorption of $CO_2$ vapor into the chemical reagent feed solution prior to flow through the membrane contactor. These results prompted the modification of the open circuit atmospheric $CO_2$ detection circuit to the configuration illustrated in FIG. 7. Two changes were incorporated into the new open circuit configuration. These were 1) storage of MEA feed solution in a gas-tight, zero headspace Tedlar bag, and 2) installation of a second in-line conductivity cell at the outlet of the MEA feed reservoir. All subsequent specific conductance measurements were taken as the differential between the two conductivity detectors.

The relative complexity of the curvilinear baseline elevation for this tracking experiment precluded the calculation of $P_{CO_2}$ from the specific conductance data as had been reported in the previous section for the closed circuit experiment using the PTFE membrane contactor. An attempt at baseline compensation was made using a quadratic equation. The resulting partially baseline compensated conductivity trace is given in FIG. 17B. While calculation of $P_{CO_2}$ from these data could not be accomplished with any degree of accuracy, the complimentary symmetry between the IR output and chemical reagent conductivity traces is taken as a strong indication of the potential for long term atmospheric $CO_2$ monitoring using the latter process. A calibration curve constructed at the outset of the tracking experiment is illustrated by the closed circles in FIG. 18.

The change in test apparatus design leading to the configuration illustrated in FIG. 7, resulted in drastically improved performance in the open circuit $CO_2$ detection equipment. The second in-line conductivity detector provided continuous monitoring of the baseline specific conductance of the MEA solution flowing into the membrane contactor. This was intended as a means of compensating for baseline elevation due to the absorption of atmospheric $CO_2$ into the MEA solution upstream of the membrane contactor. This was found to be completely unnecessary as the specific conductance at the outflow face of the MEA feed reservoir remained constant for periods of up to six weeks. The addition of the Tedlar gas-tight zero headspace bag as the MEA feed reservoir effectively prevented any undesirable contact between the MEA feed solution and atmospheric $CO_2$.

EXAMPLE 5

Figure 19:
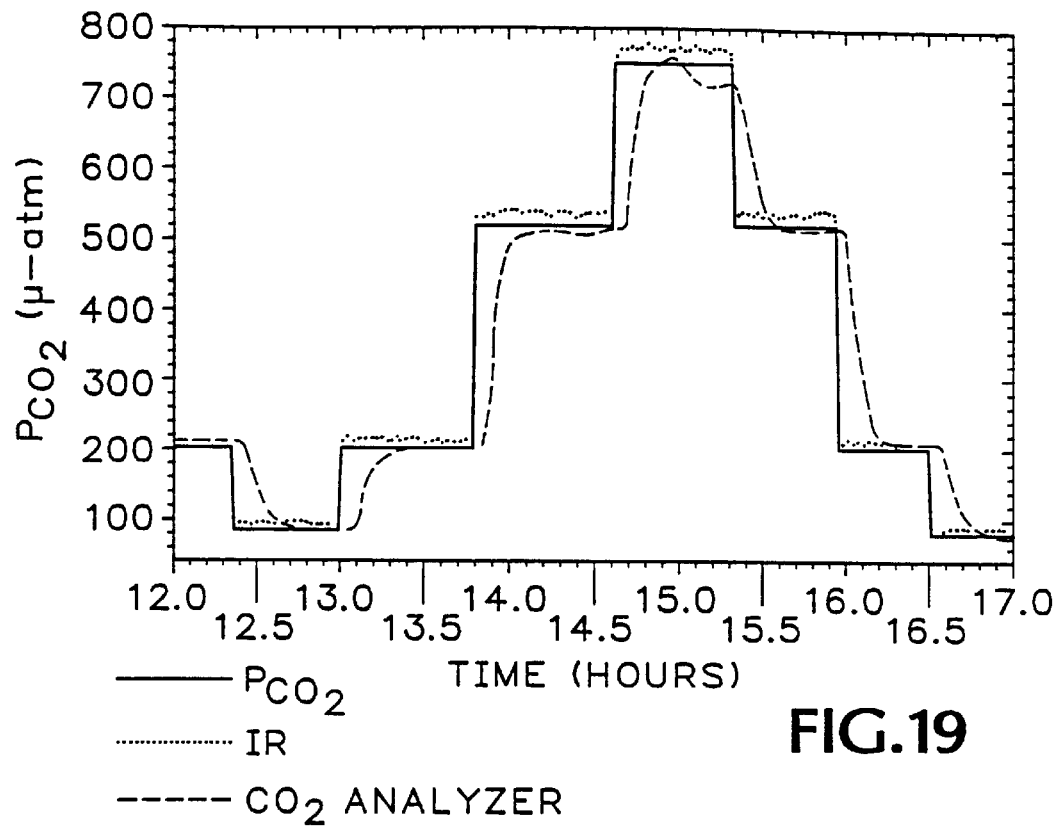
FIG. 19 is a graph showing an open circuit atmospheric $CO_2$ detection apparatus which was tested with a multiple series of calibration gases to determine precision, accuracy and the time response characteristics.

The improved open circuit atmospheric $CO_2$ detection apparatus was tested with a multiple series of calibration gases in order to determine precision, accuracy and the time response characteristics of the system. These tests took the form of step functions as illustrated in FIG. 19 for the $\mu$PP membrane contactor. Calibration air-$CO_2$ mixtures containing 80, 200, 510, and 750 were sequentially fed to the apparatus for times of approximately 45 minutes. During this time, differential specific conductance and IR derived $P_{CO_2}$ were continually monitored. Concentrations were increased stepwise from the 80 minimum to the 750 $\mu$atm maximum, and then decreased stepwise to the minimum.

Figure 20:
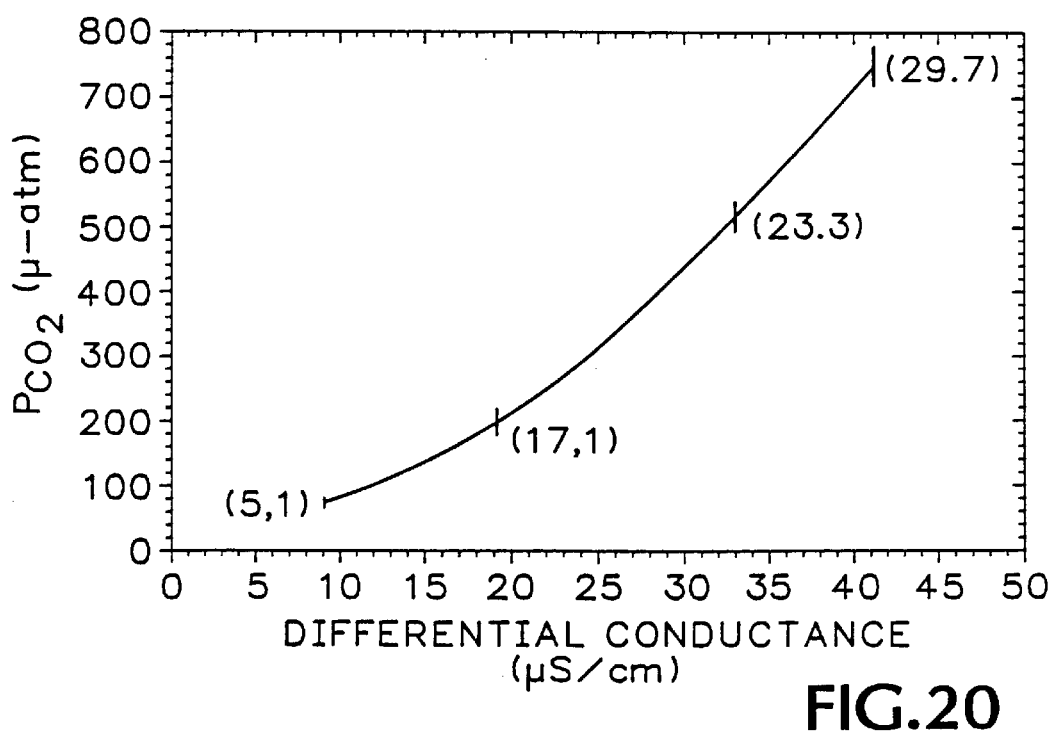
FIG. 20 is a graph showing mean specific conductances calculated for each incremental concentration step, in both ascending and descending regimes.

Mean specific conductances were calculated for each incremental concentration step, in both ascending and descending regimes. This resulted in the collection of multiple data points for each concentration. From these data a calibration curve was constructed with error bars (FIG. 20). As expected, relative standard deviations (coefficients of variation) decreased with increasing sample concentrations. The values ranged from 6.4% at 80 $\mu$atm to 4.0% at 750 $\mu$atm. Significantly, it is evident from an inspection of FIG. 19 that, with the exception of the 750 $\mu$atm concentration, once the specific conductance stabilized at the new level, the experimental apparatus gave more precise results than the IR. These experiments reflect an approximate 30-fold chemical amplification of specific conductance over distilled water values. No attempt was made to compensate for fluctuations in barometric pressure, or ambient temperature.

Figure 21:
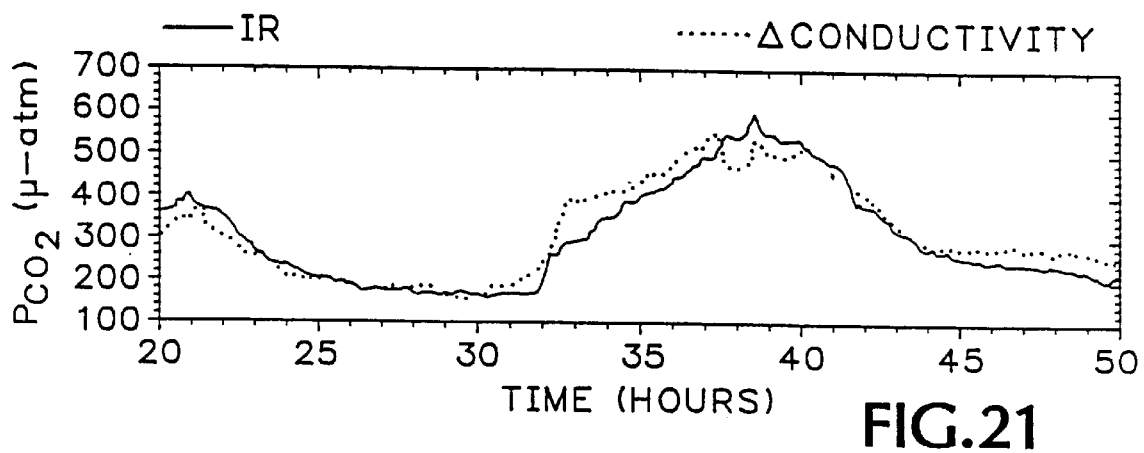
FIG. 21 is a graph showing tracking of the changes in ambient laboratory $P_{CO_2}$ over the course of approximately 50 hours for a sensor system.

Following completion of the step function standard air-$CO_2$ gas tests, the sensor system was again allowed to track the changes in ambient laboratory $PCO_2$ over the course of approximately 50 hours. The results are indicated in FIG. 21. The similarity of symmetry between the IR and experimental analyzer output is a strong indication of the potential for development of a highly accurate $P_{CO_2}$ sensor system.

EXAMPLE 6

Figure 22:
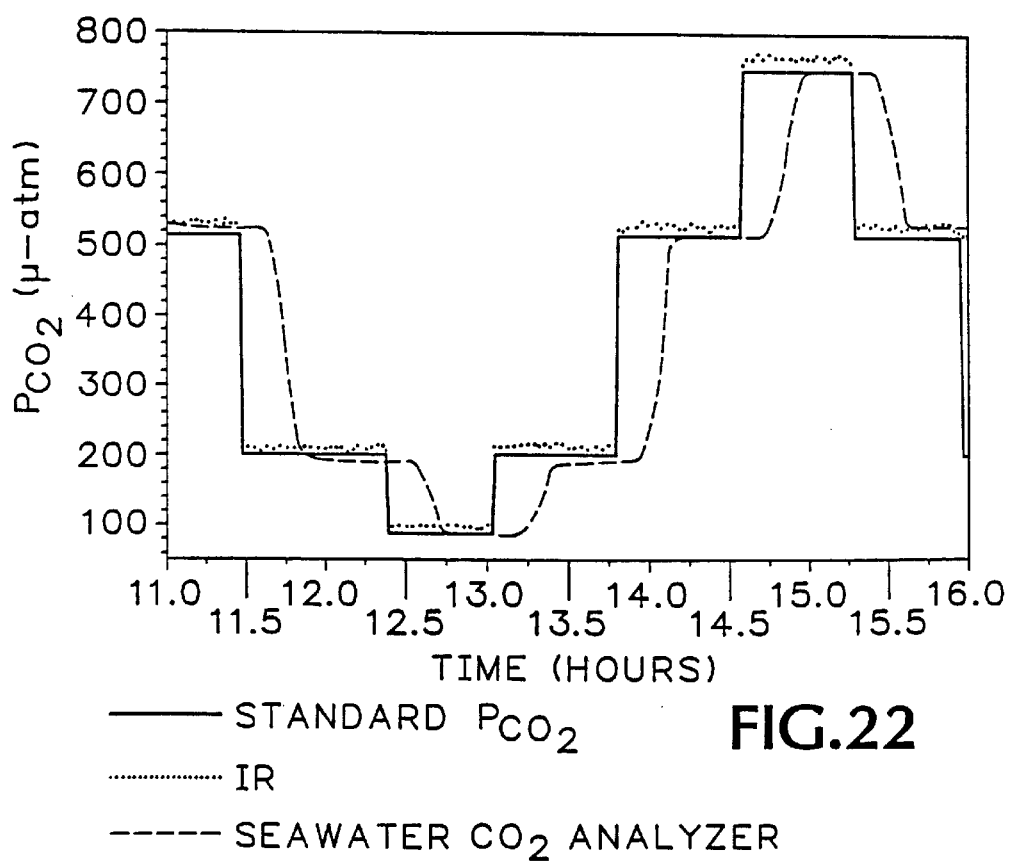
FIG. 22 is a graph showing an open circuit dissolved $CO_2$ detection apparatus which was tested with a multiple series of calibration gases to determine precision, accuracy and the time response characteristics.

This example illustrates the Open Circuit Seawater $CO_2$ Detection system. The open circuit apparatus and $\mu$PP membrane contactor used for the detection and quantitation of $CO_2$ in synthetic seawater is illustrated in FIG. 9. Preliminary shakedown of the apparatus was conducted using deionized water equilibrated with atmospheric $CO_2$ as the aqueous sample. This work generated the calibration curve shown in FIG. 18, indicating good agreement between both the atmospheric and seawater detection systems, when operated in the open circuit configuration. All subsequent aqueous phase $CO_2$ determinations were conducted using synthetic seawater Similar experiments using the standard air-$CO_2$ gas mixtures ranging in concentration between 80–750 µatm were conducted for the liquid phase detection system. The results are shown in FIG. 22. In these experiments it is noteworthy that the apparent slow response of the overall system is in reality an artifact of the means used to produce the liquid sample containing known $P_{CO_2}$ values. In this configuration, the recirculating seawater sample must first equilibrate with the standard gas before the liquid-liquid $CO_2$ exchange membrane can be expected to fully respond. Thus, the overall system response is the convolution of two dependent membrane response functions, corresponding to sample creation and analysis respectively. The overall system response time is approximately double that expected for stabilization of the transmembrane $CO_2$ transport from the synthetic brine to the MEA solution.

Figure 23:
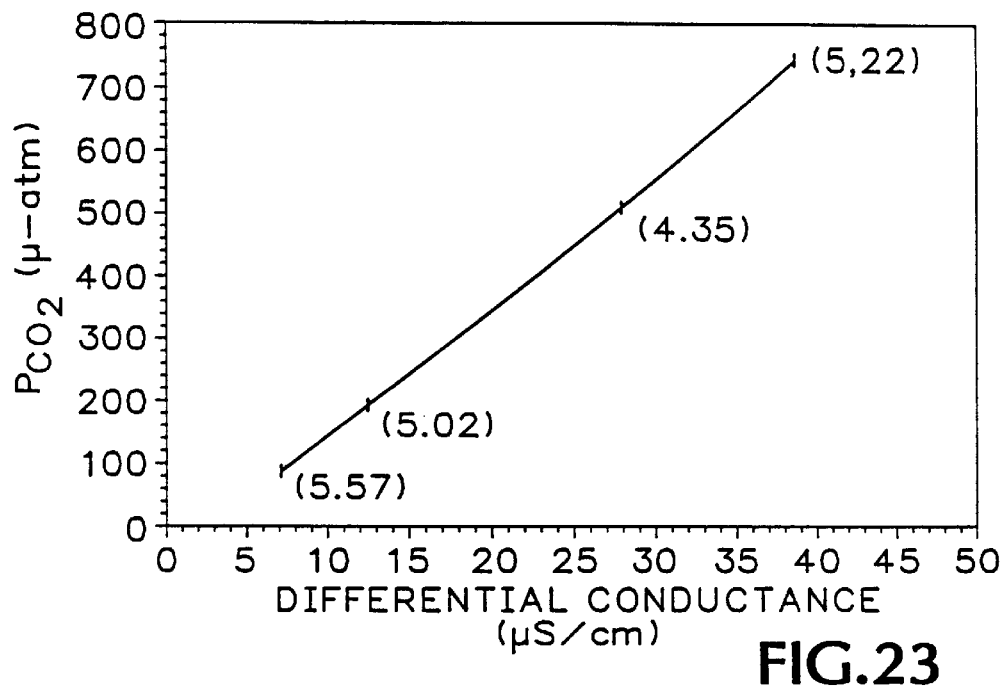
FIG. 23 is a graph showing a calibration curve and error bars from replicate determinations over the full $P_{CO_2}$ concentration range between 80–750 $\mu$atm the standard deviation of the seawater $CO_2$ analyzer.

Inspection of FIG. 22 shows a very good correspondence between the known $P_{CO_2}$ of the calibration gases and the seawater $CO_2$ analyzer output. This is also reflected in the calibration curve and error bars from replicate determinations shown in FIG. 23. Over the full $P_{CO_2}$ concentration range between 80–750 µatm the standard deviation of the seawater $CO_2$ analyzer varied between 4.35–5.57 µatm, corresponding to coefficient of variation maxima and minima of 7.0% and 0.7% respectively. These varied between 2.5% and 0.9% in the 200–500 µatm concentration range in which most real seawater values are expected to fall. Given the lack of optimization of the apparatus and processology, and the use of components such as pumps which were far from ideal in their performance, these results provide a very positive indication of the high probability that further development will result in a seawater $CO_2$ analyzer capable of providing data of the quality needed.

Figure 24:
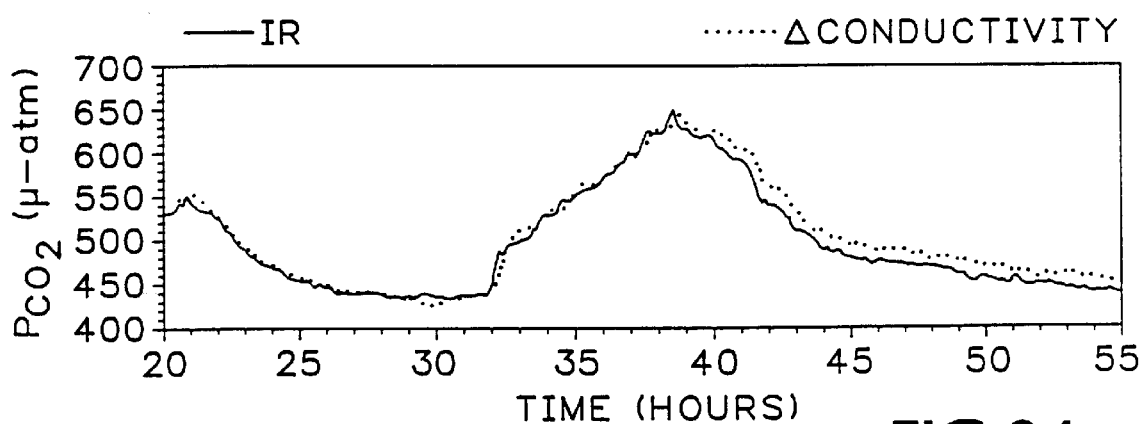
FIG. 24 is a graph showing open circuit $CO_2$ tracking of seawater.
Figure 25:
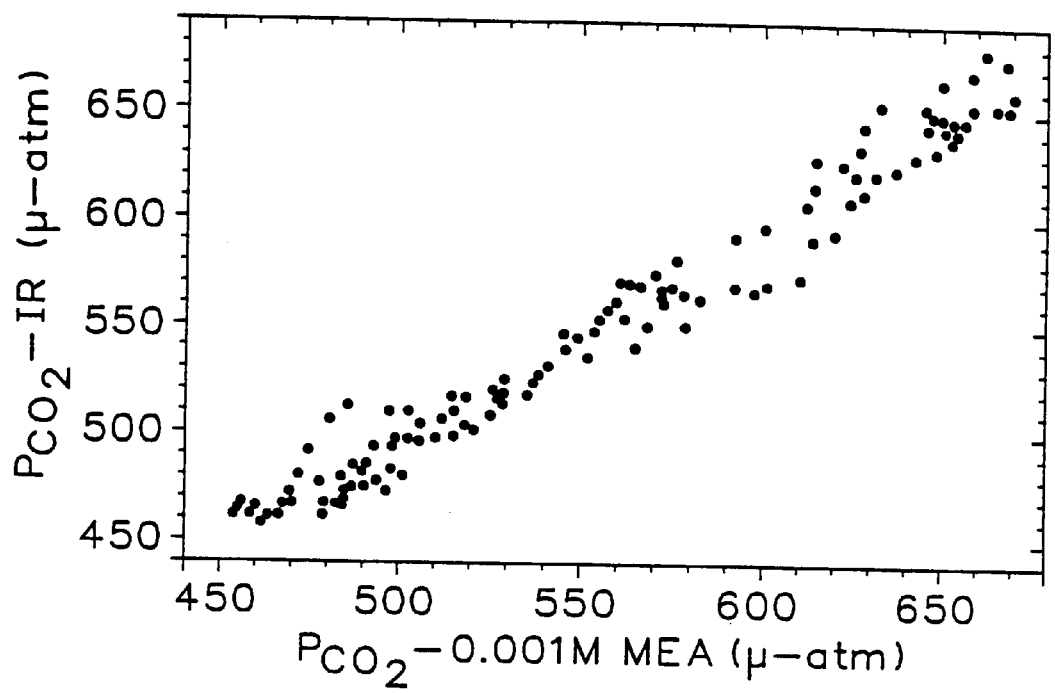
FIG. 25 is a graph showing a cross plot of IR versus $CO_2$ analyzer $P_{CO_2}$
Figure 26:
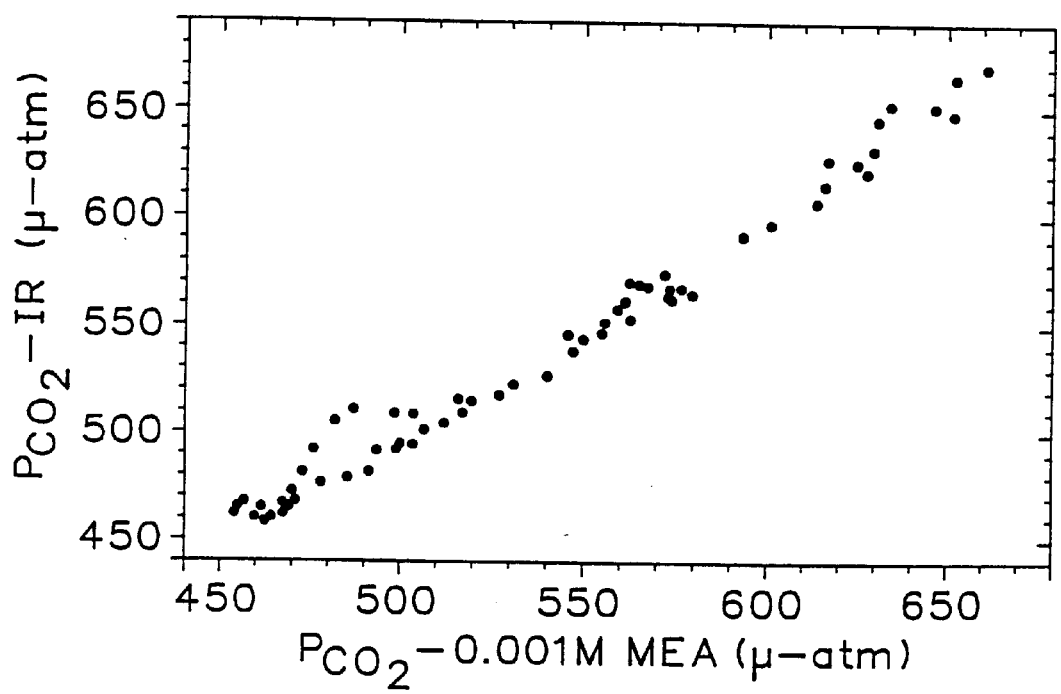
FIG. 26 is a graph showing IR and seawater analyzer $P_{CO_2}$ values over the first eighteen hours of testing.
Figure 27:
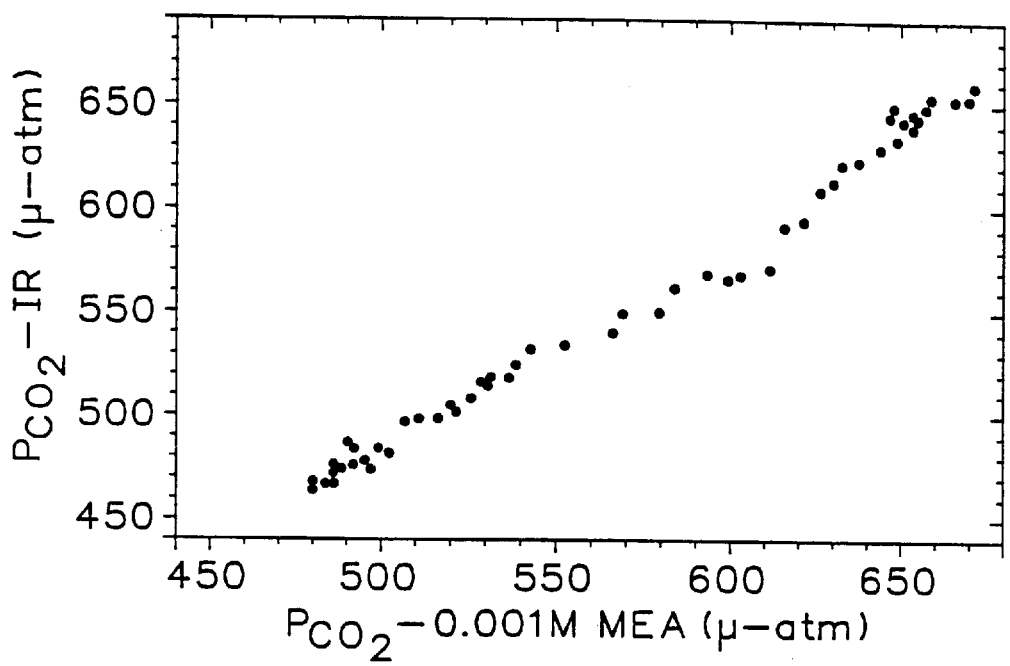
FIG. 27 is a graph showing IR and seawater analyzer $P_{CO_2}$ values after the first eighteen hours of the testing.

For a period of approximately 35 hours the open circuit seawater $CO_2$ analysis system was allowed to track the fluctuations in synthetic seawater $P_{CO_2}$ induced by the diurnal fluctuations in the ambient laboratory atmospheric $CO_2$ concentration. In this test, the synthetic seawater was first equilibrated with changing atmospheric $CO_2$. $P_{CO_2}$ in the brine was then determined by the instrument. The tracking results are given as a time series in FIG. 24 and as a cross plot of IR versus $CO_2$ analyzer $P_{CO_2}$ in FIG. 25. Very good agreement was obtained between IR and seawater analyzer $P_{CO_2}$ values over the first eighteen hours of the test (FIG. 26). After eighteen hours, the values diverged, maintaining similar symmetry, but with an offset until the conclusion of the tracking experiment (FIG. 27). The cause of the offset occurring midway through the test was found to be a change in flow rate of the chemical reagent pump of approximately 0.005 cm³/min. Future development of this technology must incorporate more reliable fluid delivery such as from syringe pumps, high performance liquid chromatography (HPLC), or osmotic pumps.

EXAMPLE 7

Stopped flow chemical reagent injection experiments were conducted to determine the role of kinetics in single pass systems, and also to evaluate a third possible configuration for both atmospheric and oceanic $CO_2$ quantitation. Using this processology a volume of chemical reagent is injected into the membrane contactor for a preset time period, after which the $CO_2$ loaded chemical reagent is pumped through an in-line conductivity cell. Detector output is in the form of a nearly gaussian peak, resulting from the "plug" of partially saturated chemical reagent solution displaced from the membrane contactor.

Figure 28:
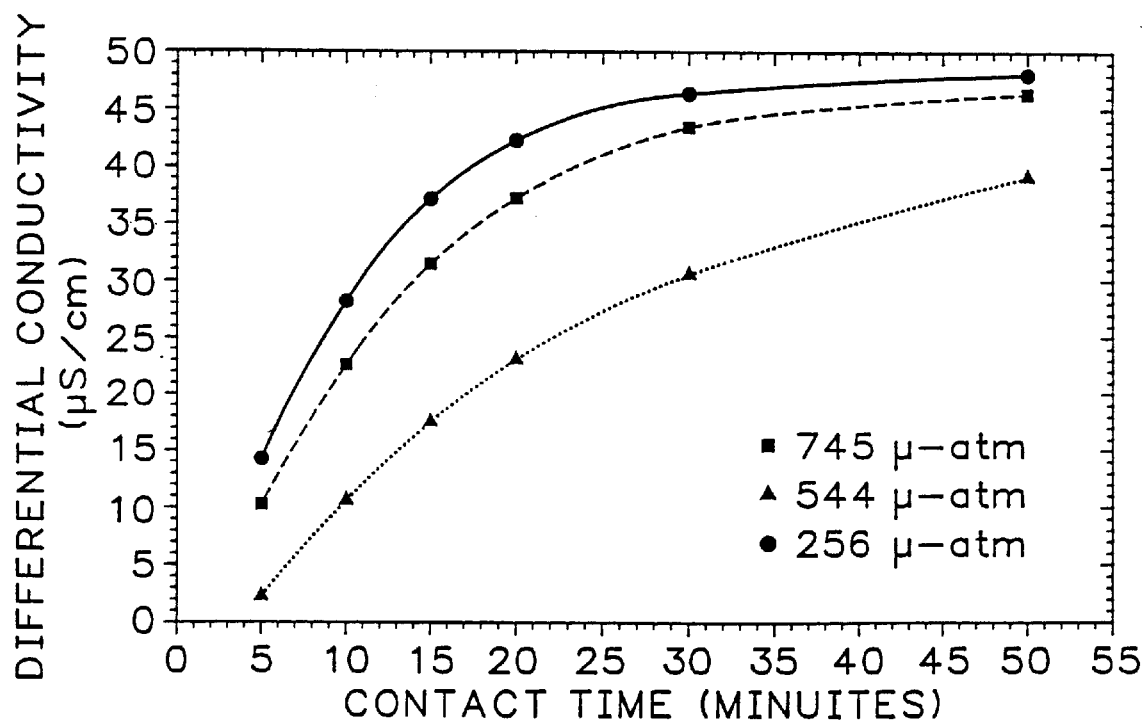
FIG. 28 is a graph showing specific conductance versus time curves for $P_{CO_2}$ values between 256–745 $\mu$atm.
Figure 29:
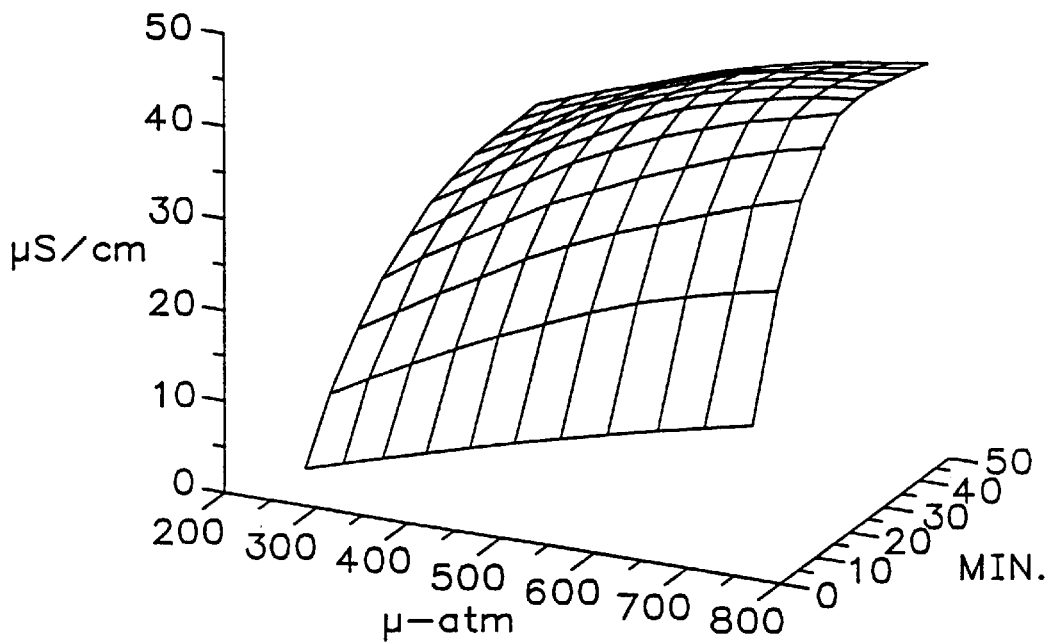
FIG. 29 is a graph showing FIG. 28 as a three dimensional surface.

The kinetics of 0.001 M MEA - $CO_2$ membrane transport and reaction was examined using aqueous $P_{CO_2}$ buffer solutions and the apparatus shown in FIG. 11. The resulting specific conductance versus time curves are shown in FIG. 28 for $P_{CO_2}$ values between 256–745 µatm., and in FIG. 29 as a three dimensional surface. The most obvious feature of this family of curves is the concentration dependence of the response rate. For high $CO_2$ concentration gradients, shorter response times were needed to approach equilibrium specific conductance values when compared to lower $CO_2$ concentration differentials.

Figure 30:
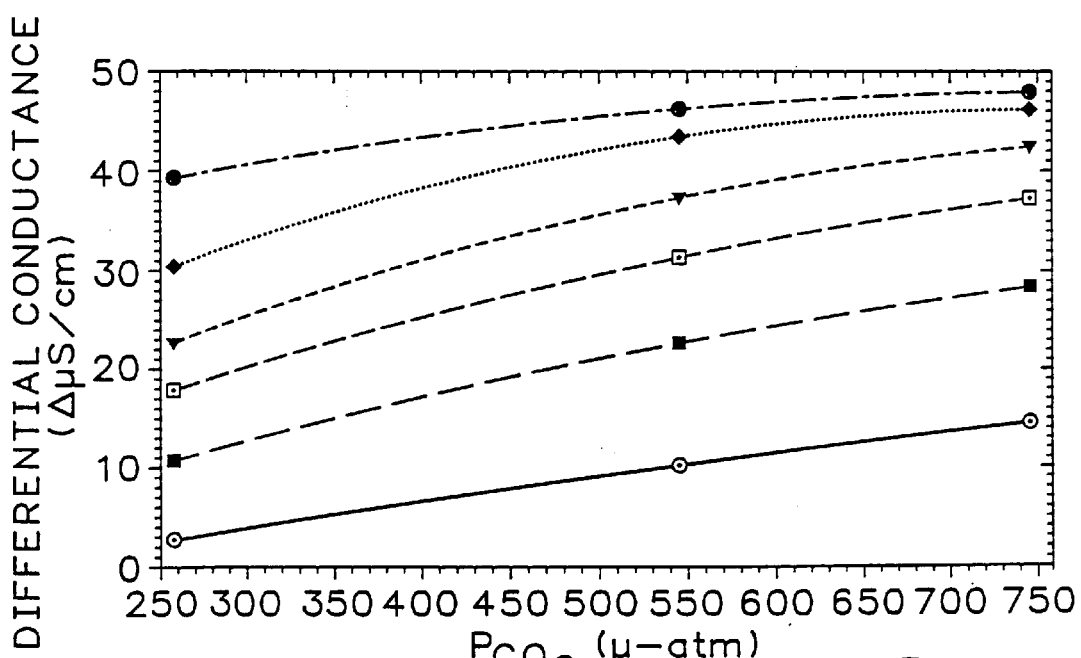
FIG. 30 is a graph showing a family of calibration curves plotted for each contact time.

These data were used to prepare the family of calibration curves shown in FIG. 30, plotted for each contact time. At a five minute contact time, the response is nearly linear. Increasing the contact time to 10 and 15 minutes increases the relative response, although at the highest $CO_2$ concentration, the curve begins to flatten. This behavior becomes even more pronounced at the longer contact times. The curvature is due to the increasing conducting species formed by the reaction of MEA with $CO_2$ as well as the degree of saturation for MEA absorption of $CO_2$. The flux of $CO_2$ across the membrane is only sufficient at the highest $CO_2$ concentration gradients and the longest contact times to saturate the MEA. As the concentration of ionic species increases, activity coefficients and hence equivalent conductances ($\Lambda_L$) of the protonated amine, carbamate, bicarbonate, and carbonate decrease due to ion-ion interaction. This results in diminished differential specific conductance response at higher $P_{CO_2}$.

When the chemical reagent injection contact times were extended to much longer times (i.e. 60–300 minutes), the 745 and 256 µatm curves approached a constant differential conductance. In this situation the individual specific conductances continued to increase with time. This behavior is due to the flux of water across the membrane. The differences in osmotic pressure between the MEA and buffer solutions drive the transfer of water from the MEA solution to the $PCO_2$ buffer. This results in an increase in MEA concentration.

EXAMPLE 8

Seven replicate injections of the three standard buffers were made at the 30 minute contact time. These data were used to construct the calibration curve with error bars shown in FIG. 31. The standard deviations for the 256, 544, and 745 µatm buffers are 1.49, 9.91, and 21.85 µatm respectively. The standard deviation as a function of $P_{CO_2}$ is an increasing exponential relation of the form, $$\sigma = -4.76 + 2.93 \exp(0.00296\ P_{CO_2}),$$

with a correlation coefficient ($r^2$) of 1.0000. Using this expression to evaluate σ at a partial pressure of 350 µatm yields σ=3.5 µatm.

Figure 32:
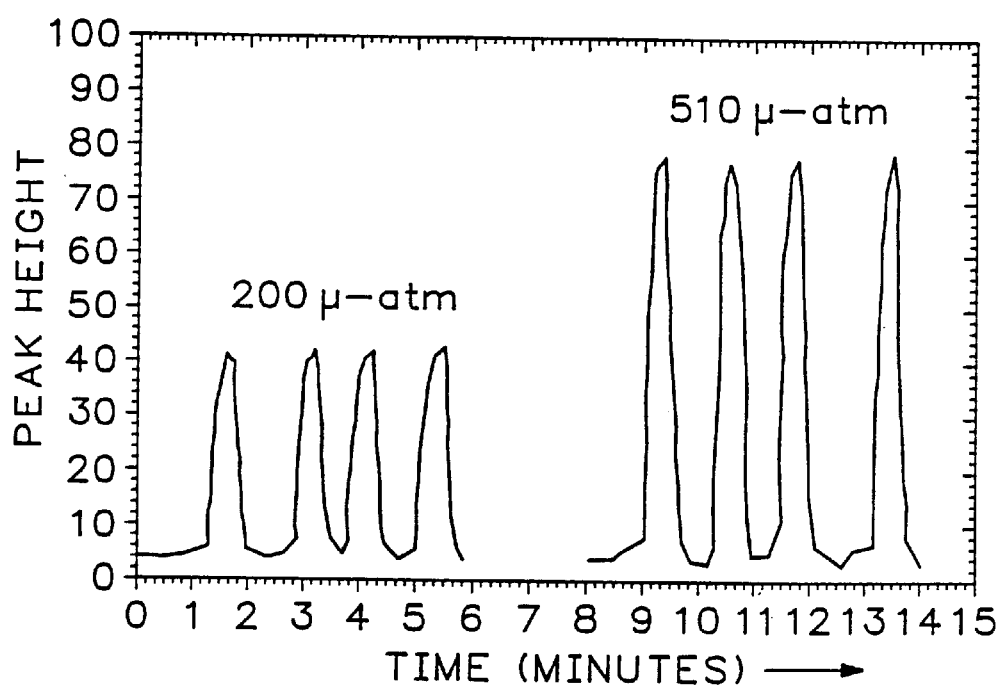
FIG. 32 is a graph showing synthetic seawater equilibrated with a known $P_{CO_2}$ at a contact time of 30 minutes.

The chemical reagent injection procedure was also used with synthetic seawater samples equilibrated with a known $P_{CO_2}$ at a contact time of 30 minutes. The peak heights for replicate injections at values of 200 and 510 µatm $P_{CO_2}$ are shown in FIG. 32. This process clearly shows promise as a means of obtaining precise quantitation of oceanic $P_{CO_2}$.

EXAMPLE 9

Figure 33:
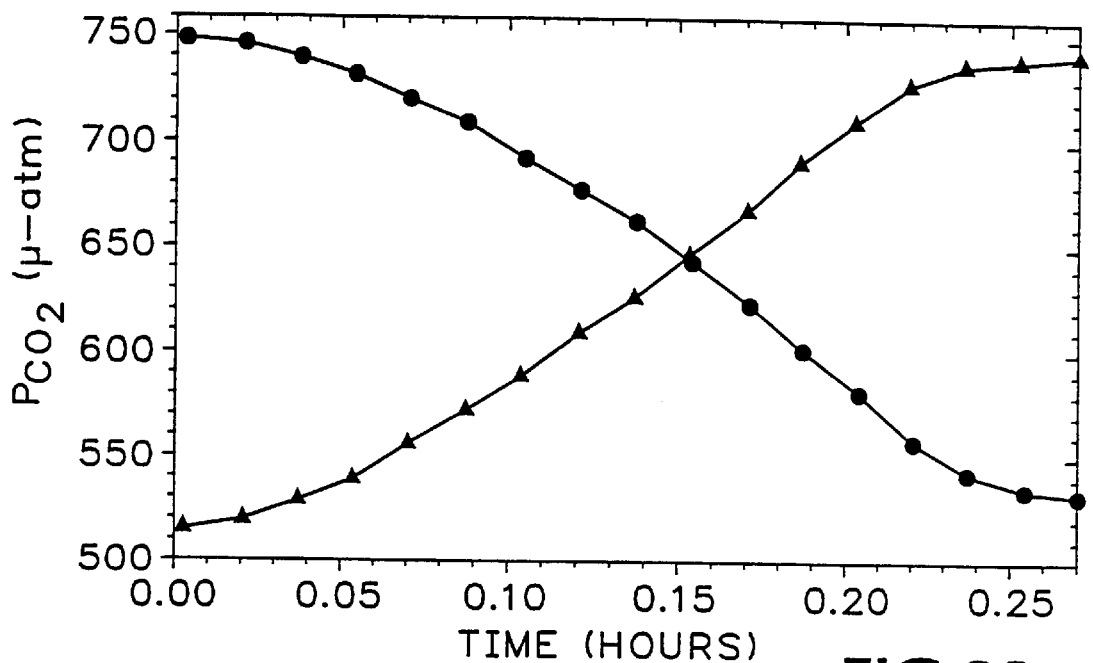
FIGS. 33–35 are analyzer time responses to standard $P_{CO_2}$ step functions summarized in FIGS. 19, and 22 for atmospheric and oceanic open circuit $CO_2$ analyzer configurations respectively.
Figure 34:
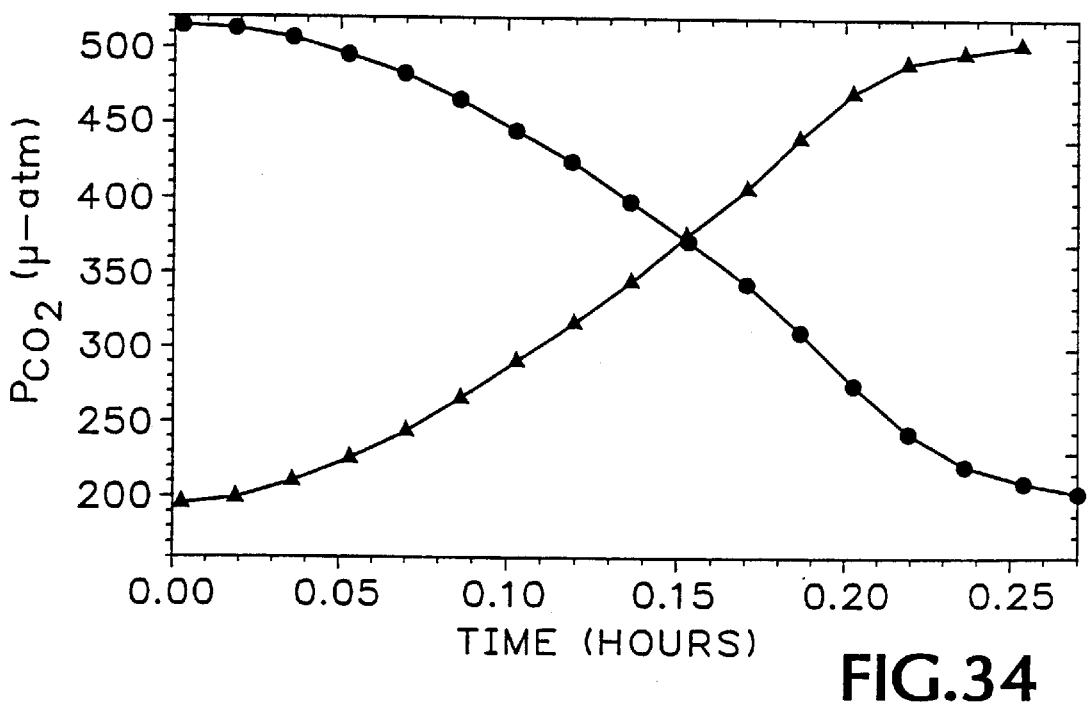
Figure 35:
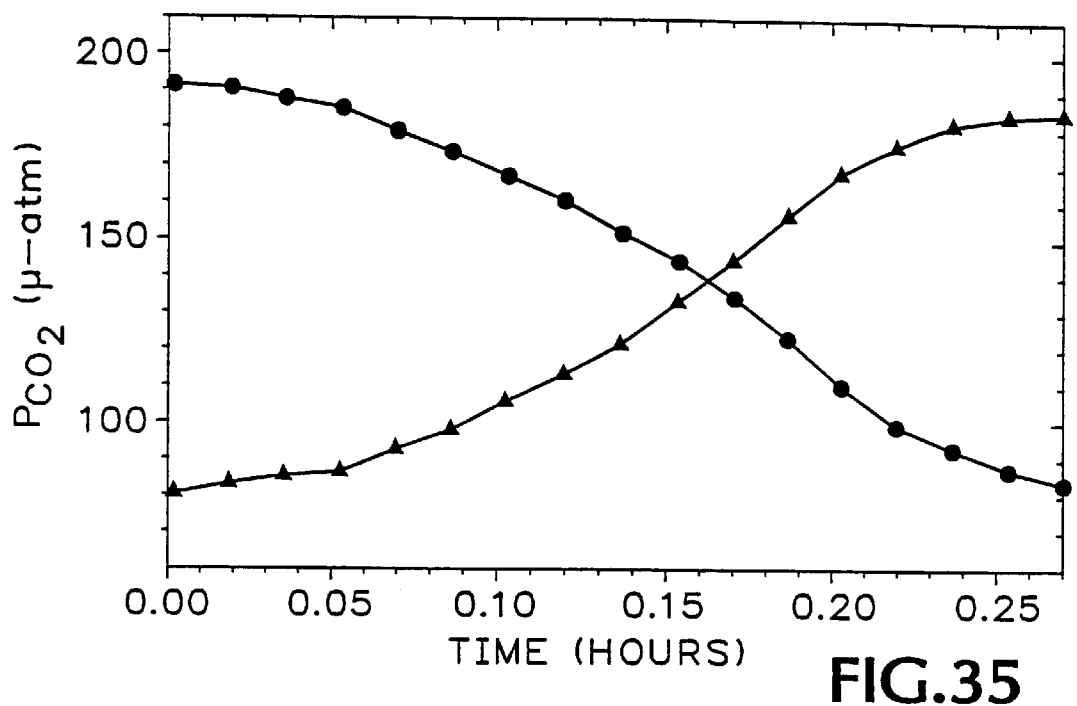

The analyzer time responses to standard $P_{CO_2}$ step functions summarized in FIGS. 19, and 22 for atmospheric and oceanic open circuit $CO_2$ analyzer configurations respectively and presented in greater detail in FIGS. 33–35 for the latter configuration, indicate equivalent response characteristics irrespective of whether the $P_{CO_2}$ values are increasing or decreasing. The response times also were found to be relatively independent of the concentration differences between initial and final conditions. The response times shown for the seawater $CO_2$ analyzer are prolonged by an undetermined factor, owing to the process used for equilibrating the synthetic seawater with atmospheric $P_{CO_2}$.

EXAMPLE 10

Figure 36:
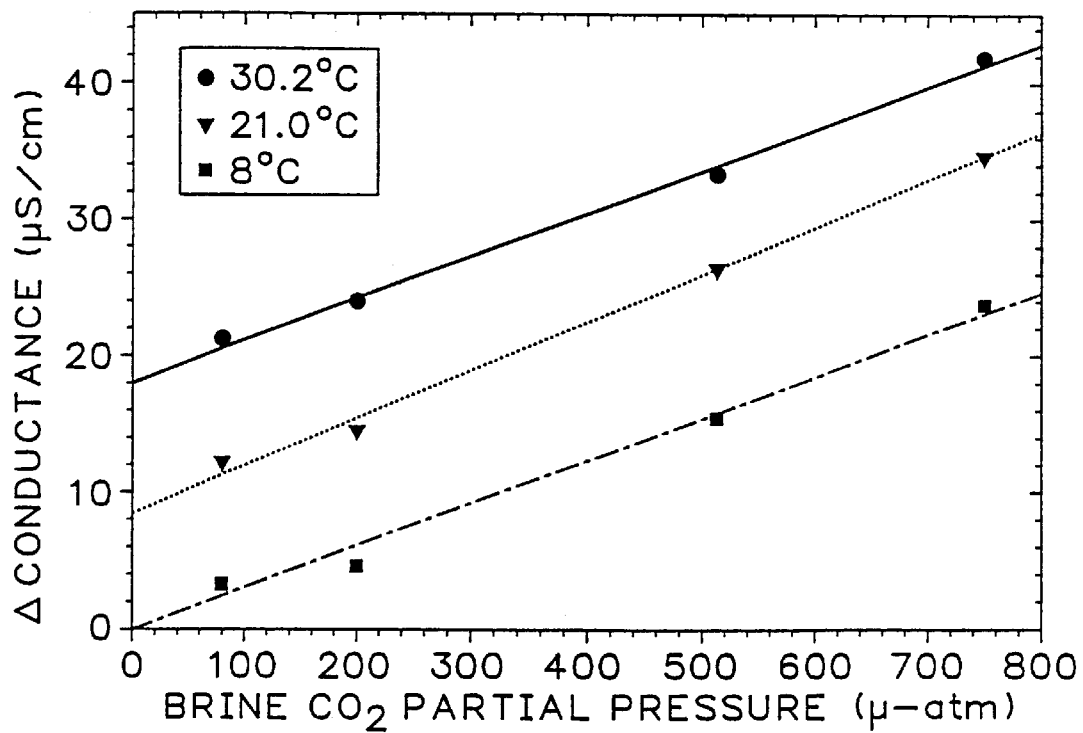
FIG. 36 is a graph showing an open circuit seawater $CO_2$ apparatus used to determine variations in instrument response to aqueous levels between 80–750 $\mu$atm, at 8, 21, and 30° C. and presented as a family of curves.
Figure 37:
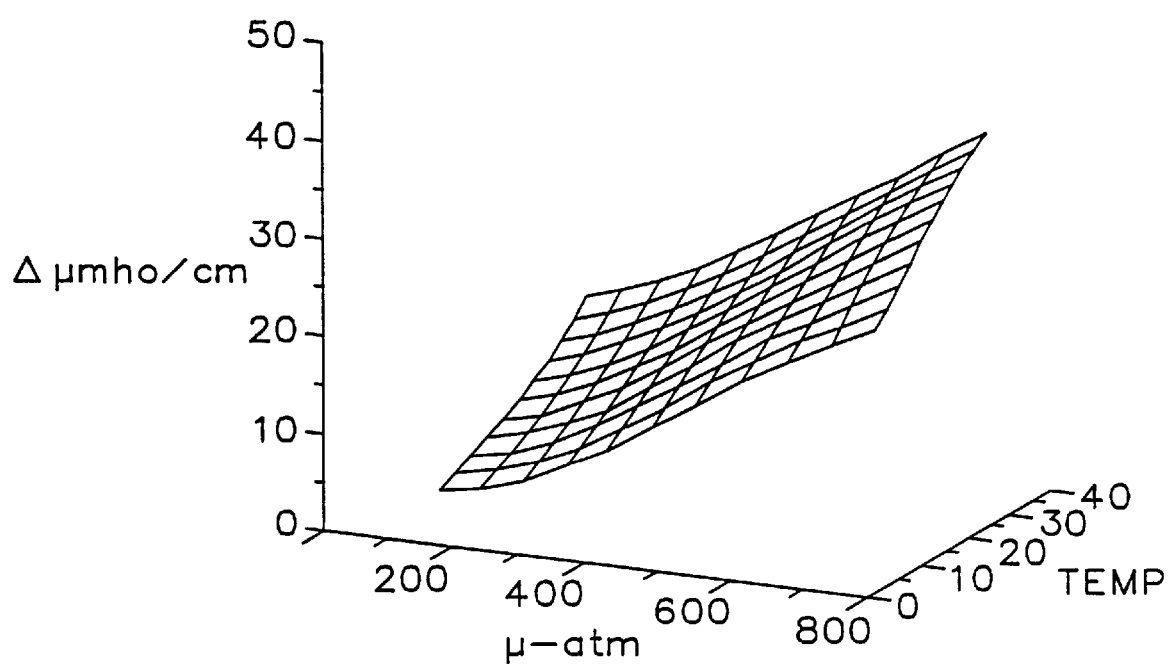
FIG. 37 is the data of FIG. 36 presented as a three dimensional surface.

An open circuit seawater $CO_2$ apparatus was used to determine variations in instrument response to aqueous levels between 80–750 µatm, at 8, 21, and 30° C. The experimental results are presented as a family of curves in FIG. 36, and as a three dimensional surface in FIG. 37. Not surprisingly, the specific conductance associated with any given $P_{CO_2}$ value rises with increasing temperature. The measured differences in specific conductance are significant over relatively small temperature changes. From these data it is very clear that precise temperature measurement, and means of temperature compensation must be incorporated into the device.

EXAMPLE 11

Three acid gases were investigated for interference with the subject processology: HCl, $SO_2$, and NO. The experimental results are summarized in Table I. Two of these substances, $SO_2$ and NO, were found to be strongly interfering. These gases readily transported across the membrane, and formed ionic species by the following reactions:

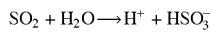

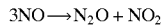

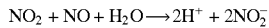

The interference noted is due to the formation of completely dissociated strong mineral acids. Because these species form ionic and hence non-membrane transportable species in aqueous solution, they should not exhibit a significant interference when aqueous phase samples are analyzed.

EXAMPLE 12

A packed bed of calcite crystals ($CaCO_3$) was evaluated as a potential source of in-line calibration for the chemical reagent based $CO_2$ analyzer. Such a bed will impart a controllable amount of $CO_3=$ to the effluent. A molybdenum trioxide based solid phase acidifier, also incorporating proprietary technology, was located immediately downstream to shift the inorganic carbon equilibria from $CO_3=$ and $HCO_3-$ toward $CO_2$. In a gas free and gas-tight environment, DI water was pumped through the solid state modules and into an open circuit dissolved $CO_2$ detection apparatus flowing 0.001 M MEA solution. The experimental results are summarized in Table II. The calibration system produced an aqueous inorganic carbon concentration of 1.4 mg/L (as C), and resulted in a differential specific conductance signal of 22.5 µS/cm. Inspection of the calibration curve shown in FIG. 23 indicates that this value corresponds to a $P_{CO_2}$ of approximately 450 µatm. This preliminary result is encouraging. With the use of carbonate species of differing solubilities, the subject solid phase modules can be made to produce the desired range of aqueous $P_{CO_2}$.

Regarding Examples 1–13, the quantitative determination of $CO_2$ in atmospheric and aqueous samples using membrane transport, chemical reagent induced chemical amplification, and conductivity detection has been demonstrated. Three chemical reagent flow configurations have been evaluated: closed circuit with continuous chemical reagent recirculation, open circuit with continuous chemical reagent flow in a single pass through the membrane contactor, and stopped flow chemical reagent injection.

Three membrane materials were evaluated. These included nonporous polytetrafluoroethylene (PTFE), polydimethylsiloxane (Siloxane), and microporous polypropylene (µPP). Microporous polypropylene hollow fibers proved to be the most preferred, primarily due to high $CO_2$ transport rates and large surface area to volume ratio. The most useful configuration for the hollow fiber membrane contactor was found to be the coaxial tube within a tube arrangement for both gas-liquid and liquid-liquid $CO_2$ exchange.

Primary, secondary, and tertiary alkanolamines with two and three carbon alkanol groups were evaluated for conductivity response, reversibility of $CO_2$ absorption, and concentration effects. Monoethanolamine (MEA) was identified as the most preferred alkanolamine based on specific conductance changes corresponding to a fixed $P_{CO_2}$. Diethanolamine (DEA) and diisopropanolamine (DIPA) were found to be the most readily reversible of the alkanolamines tested. DEA was selected for use in the closed loop detector configuration. MEA was used in the open circuit and stopped flow chemical reagent injection configurations, since reversibility is not required.

The chemical reagent concentration determines the total $CO_2$ absorption capacity of the solution. The specific conductance of the chemical reagent solution is directly but non-linearly proportional to the quantity of $CO_2$ absorbed. The deviation from linearity in the detector calibration curves are due to the combined effects of membrane transport rates, ionization reaction kinetics, the degree of saturation of the chemical reagent solution, decreased activity coefficients at higher concentrations, and the multiple equilibria associated with $CO_2$ dissolution and the formation of ionic species. Contact times and chemical reagent concentrations are the two prime variables which can be manipulated to shift the desired dynamic $P_{CO_2}$ range of the analyzer into the steep and nearly linear portion of the calibration curve. This allows optimal precision and accuracy to be attained.

For a given continuous flow open loop membrane contactor, contact time varies with the chemical reagent flow rate. Chemical reagent flow rates of approximately 0.01 mL/min were used. The peristaltic pumps available for the feasibility demonstration were not capable of providing constant flows at these low rates. Very significant improvements in precision and accuracy of the $CO_2$ analyzer can be expected from the use of more sophisticated low flow rate pumping systems such as syringe pumps, HPLC pumps, or osmotic pumps.

Contact time in the stopped flow chemical reagent injection analyzer configuration is controlled by clock and can be expected to be accurately controlled by a microcontroller or microcomputer. Using 0.001 M MEA, valid calibrations were obtained over a range of contact times between 5 and 30 minutes. For a given membrane contactor design, contact time and MEA concentration can be optimized to provide the highest level of accuracy for the range of interest. Short contact times require more accurate timing of events than do longer times.

Temperature influences diffusion, dissolution, and reaction rates. Temperature also affects $CO_2$ solubility, ionization reaction equilibria, and equivalent conductances of all ionic species. Improved detector performance can be obtained by incorporation of a highly accurate temperature measurement device, such as an RTD, into the $CO_2$ analyzer design. A temperature compensation algorithm is required to correct detector response for the changes in analyzer performance associated with temperature fluctuations of the operational environment.

Interferences from acid gases such as NO and $SO_2$ were evident for the atmospheric $CO_2$ detector. These interferences are due to the formation of completely dissociated strong mineral acids which are highly conductive. Because these gases form ionic species in aqueous solutions, they are not amenable to vapor phase membrane transport, and hence are not expected to interfere with the determination of $CO_2$ in seawater.

Remote calibration capability for a buoy mounted analyzer greatly improves system accuracy over prolonged periods of deployment. The controlled dissolution of crystalline $CaCO_3$ packed into a flow-through module, acidification of the stream using a similar bed of crystalline $MoO_3$, and membrane transport of the resulting $CO_2$ has been shown to produce a specific conductance response equivalent to a $P_{CO_2}$ of approximately 450 µatm.

Figure 18:
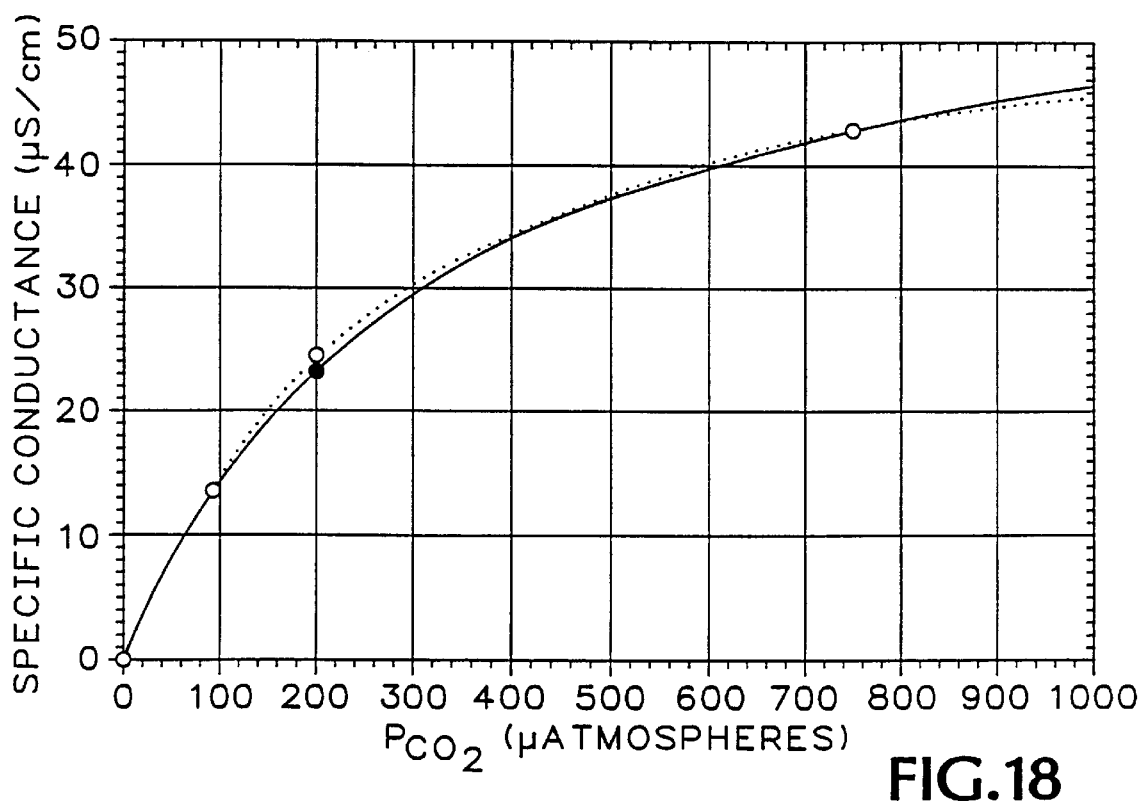
FIG. 18 is a graph showing a calibration curve constructed at the outset of the tracking experiment.

The open circuit analyzer configuration yielded a precision of ±4–5 µatm (1 σ) between 80 and 750 µatm $P_{CO_2}$ for synthetic seawater samples, and ±5–30 µatm for this range of $P_{CO_2}$ in air. The open circuit analyzer is capable of tracking $CO_2$ fluctuations in air and water for extended periods of continuous operation. Important factors for establishing open circuit analyzer configuration include: precise control of flow rates, compensation for temperature and pressure effects, and optimization of the chemical reagent concentration so that $P_{CO_2}$ lies within the steep and nearly linear portion of the $P_{CO_2}$ versus specific conductance curve (FIG. 18).

Response times of approximately 15 minutes were obtained for step function changes in $P_{CO_2}$. This value can be improved upon through optimization of the mass transport characteristics of the membrane contactor. Significantly, $P_{CO_2}$ values provided by the open circuit $CO_2$ analyzer followed the known concentrations of standard $CO_2$-air mixtures during step changes more accurately than did our non-dispersive IR detector. The sensitivity of the open circuit $CO_2$ analyzer can be attributed to the substantial chemical amplification of the conductivity signal. The specific conductance of deionized water equilibrated with an atmospheric $P_{CO_2}$ of 350 µatm is approximately 0.9 µS/cm, while a 0.001 M MEA solution in the open circuit configuration exposed to 350 µatm has a differential specific conductance of approximately 32 µS/cm, corresponding to a 35-fold amplification.

Figure 31:
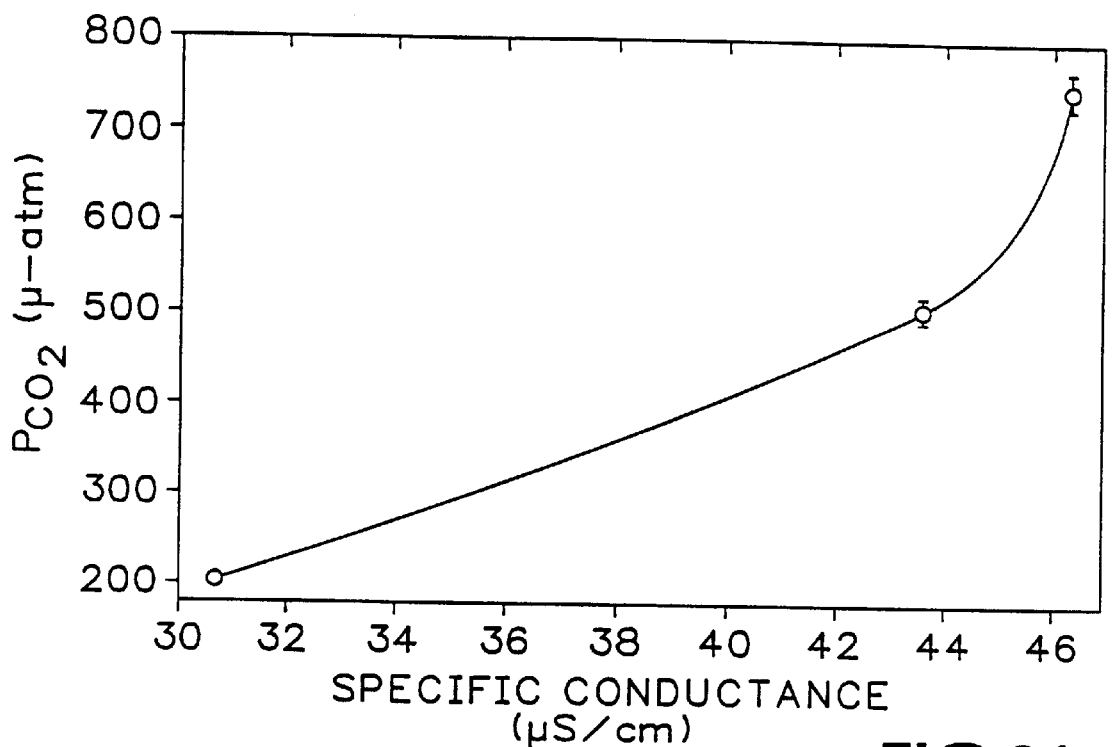
FIG. 31 is a graph showing seven replicate injections of the three standard buffers were made at the 30 minute contact time and used to construct a calibration curve with error bars.

In this case, the standard deviation increased exponentially with concentration. Based upon this relationship, approximate error values for 350 µatm $P_{CO_2}$ of ±3.5 µatm were obtained. Performance of the chemical reagent injection $CO_2$ analyzer configuration can be improved significantly through temperature and pressure compensation, and optimization of the chemical reagent molarity and contact time to shift the desired $CO_2$ concentration range into the linear portion of the calibration curve (FIG. 31). Response times of the stopped flow analyzer were between 5 and 30 minutes.

An attractive feature of the open circuit configuration is operational simplicity and the consequent ease of operational control. The stopped flow configuration offers potential gains in decreased chemical reagent consumption rates, more precise contact time control, and relaxed flow control requirements. Both configurations are compatible with long term deployment for prolonged periods of unattended operation. The chemical reagent flow rates used in the open circuit configuration are extremely low. $CO_2$ analyzer footprint, weight, and power requirements are preferably 0.014–0.028 $m^3$ (0.5–1.0 $ft^3$), 6.8–9 kg (15–20 lbs), and 10–20 W, respectively.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

We claim:

1. A process for determining the concentration of $CO_2$ or partial pressure of $CO_2$ in a seawater or water sample, which comprises:

providing a control solution, including an alkanolamine chemical reagent, that absorbs large quantities of $CO_2$ by a reversible reaction with $CO_2$ producing conductive ionic $CO_2$ reaction products;

providing a membrane contactor having a membrane located therewithin for separating said seawater or water sample and said control solution, said membrane being permeable to $CO_2$ but impermeable to conductive ionic $CO_2$ reaction products;

measuring the specific conductance of the control solution before exposure to $CO_2$;

introducing said seawater or water sample and said control solution into said membrane contactor, the seawater or water sample flowing through the membrane contactor on the opposite side of the membrane from the control solution;

transporting $CO_2$ from said seawater or water sample through the membrane into said control solution;

chemically amplifying conductive species in the said control solution through reversible reactions between $CO_2$ and the chemical reagent which produces said conductive ionic $CO_2$ reaction products;

measuring the specific conductance of the control solution including said conductive ionic $CO_2$ reaction products; and determining partial pressure of $CO_2$ or $CO_2$ concentration in the seawater or water sample by comparing the difference between the specific conductance of the control solution including said conductive ionic $CO_2$ reaction products and the specific conductance of the control solution before exposure to $CO_2$, and comparing this difference to known partial pressure of $CO_2$ or $CO_2$ calibration values.

2. The process of claim 1, wherein the membrane is a microporous membrane or a non-porous membrane.

3. The process of claim 1, wherein the seawater or water sample and the control solution flow counter-currently to each other within the membrane contactor, thereby maximizing the $CO_2$ concentration difference along the membrane contactor, and the passage of $CO_2$ into the control solution.

4. The process of claim 1, wherein the membrane materials for the non-porous membranes comprise polytetrafluoroethylene, polydimethylsiloxane, and the membrane material for the microporous materials is microporous polypropylene.

5. The process of claim 1, wherein the membrane is a microporous membrane comprising hollow fibers.

6. The process of claim 5, wherein the hollow fibers comprise a coaxial tube within a tube arrangement for both gas-liquid and liquid-liquid $CO_2$ exchange.

7. The process of claim 1, wherein the specific conductance is measured by a flow-through instrument.

8. The process of claim 1, wherein the process is continuous.

9. The process of claim 1, wherein the specific conductance of the control solution is detected using an conductivity measuring instrument.

10. The process of claim 2, wherein the seawater contains up to 36 parts per thousand of NaCl by weight.

11. The process of claim 1, wherein the alkanolamine is selected from a group consisting of primary, secondary, and tertiary alkanolamines.

12. The process of claim 1, wherein the alkanolamine is selected from a group consisting of diethanolamine, monoethanolamine, triethanolamine, N,N-dimethylethanolamine, N-methylethanolamine, N-ethylethanolamine, and diisopropanolamine.

13. The process of claim 1, wherein the concentration of the conductive ionic $CO_2$ reaction products are increased by at least about a factor of 25 fold as compared to $CO_2$ reaction products formed without amplification.

14. The process of claim 1, which comprises a closed circuit configuration in which the control solution continuously recirculates through the membrane contactor reversibly gaining or losing $CO_2$ from the seawater or water sample, depending on the $CO_2$ concentration gradient across the membrane, giving rise to specific conductance in the control solution as the chemical reagent reversibly reacts with $CO_2$ which are proportional to the partial pressure of $CO_2$ the sample phase.

15. The process of claim 1, which comprises an open circuit configuration in which chemical reagent solution flows from a feed reservoir, first through the membrane, then measuring the specific conductance of the control solution including said conductive ionic $CO_2$ reaction products, and then to a waste repository, the chemical reagent being expendable and making a single pass through the system.

16. The process of claim 1, which comprises a stopped flow injection configuration in which the chemical reagent is injected into the membrane contactor, the flow is stopped, and after a predetermined contact time, flow is re-established, a plug of $CO_2$-containing chemical reagent solution being displaced from the membrane, and then measuring the specific conductance of the control solution including said conductive ionic $CO_2$ reaction products.

17. A process for continuously determining the concentration of $CO_2$ or partial pressure of $CO_2$ in a seawater or water sample, which comprises:

providing a control solution, including an alkanolamine chemical reagent selected from a group consisting of primary, secondary, and tertiary alkanolamines, that absorbs large quantities of $CO_2$ by a reversible reaction with $CO_2$ producing conductive ionic $CO_2$ reaction products;

providing a membrane contactor having a membrane located therewithin for separating said seawater or water sample and said control solution, said membrane being permeable to $CO_2$ but impermeable to conductive ionic $CO_2$ reaction products;

continuously measuring the specific conductance of the control solution before exposure to $CO_2$ using a flow-through instrument;

continuously introducing said seawater or water sample and said control solution into said membrane contactor, the seawater sample flowing through the membrane contactor on the opposite side of the membrane from the control solution;

continuously transporting $CO_2$ from said seawater or water sample through the membrane into said control solution;

continuously chemically amplifying conductive species in the control solution through reversible reactions between $CO_2$ and the chemical reagent which produce said conductive ionic $CO_2$ reaction products, the conductive ionic $CO_2$ reaction products being increased by at least about a factor of 25 fold as compared to $CO_2$ reaction products formed without amplification;

continuously measuring the specific conductance of the control solution including said conductive ionic $CO_2$ reaction products using a flow-through instrument; and continuously determining partial pressure of $CO_2$ or $CO_2$ concentration in the seawater or water sample by comparing the difference between the specific conductance of the control solution including said conductive ionic $CO_2$ reaction products and the specific conductance of the control solution before exposure to $CO_2$, and comparing this difference to known partial pressure of $CO_2$ or $CO_2$ calibration values.

18. A process for continuously determining the concentration of $CO_2$ or partial pressure of $CO_2$ in a seawater or water sample, which comprises:

providing a control solution, including an alkanolamine chemical reagent, that absorbs large quantities of $CO_2$ by a reversible reaction with $CO_2$ producing conductive ionic $CO_2$ reaction products;

providing a membrane contactor having a membrane located therewithin for separating said seawater sample and said control solution, said membrane being permeable to $CO_2$ but impermeable to conductive ionic $CO_2$ reaction products;

continuously measuring the specific conductance of the control solution before exposure to $CO_2$ using a flow-through instrument;

continuously introducing said seawater or water sample and said control solution into said membrane contactor, the seawater or water sample flowing through the membrane contactor on the opposite side of the membrane from the control solution;

continuously transporting $CO_2$ from said seawater or water sample through the membrane into said control solution;

continuously chemically amplifying conductive species in the control solution through reversible reactions between $CO_2$ and the chemical reagent which produce said conductive ionic $CO_2$ reaction products;

continuously measuring the specific conductance of the control solution including said conductive ionic $CO_2$ reaction products using a flow-through instrument; and continuously determining partial pressure of $CO_2$ or $CO_2$ concentration in the seawater or water sample by comparing the difference between the specific conductance of the control solution including said conductive ionic $CO_2$ reaction products and the specific conductance of the control solution before exposure to $CO_2$, and comparing this difference to known partial pressure of $CO_2$ or $CO_2$ calibration values.

* * * * *